US006368787B1

(12) United States Patent
Yeh et al.

(10) Patent No.: US 6,368,787 B1
(45) Date of Patent: Apr. 9, 2002

(54) METHODS AND COMPOSITIONS FOR IDENTIFYING MORPHOGENIC PROTEIN ANALOGS USING MORPHOGENIC PROTEIN RESPONSIVE INHIBITORY ELEMENTS

(75) Inventors: Lee-Chuan C. Yeh; John C. Lee, both of San Antonio, TX (US)

(73) Assignee: Stryker Corporation, Kalamazoo, MI (US)

( * ) Notice: Subject to any disclaimer, the term of this patent is extended or adjusted under 35 U.S.C. 154(b) by 0 days.

(21) Appl. No.: 09/465,353

(22) Filed: Dec. 16, 1999

(51) Int. Cl.[7] ............................. C12Q 1/60; C07K 1/00; C12P 21/06; C07H 19/00; A01N 43/04
(52) U.S. Cl. ......................... 435/4; 530/350; 530/395; 530/840; 435/69.1; 435/440; 435/320.1; 435/252.3; 424/423; 536/22.1; 514/44; D24/155
(58) Field of Search ................................. 530/350, 395, 530/840; 435/4, 69.1, 440, 320.1, 252.3; 424/423; 536/22.1; 514/44; D24/155

(56) References Cited

U.S. PATENT DOCUMENTS

| 4,975,526 A | 12/1990 | Kuberasampath et al. .. 530/350 |
| 5,162,114 A | 11/1992 | Kuberasampath et al. .. 424/423 |
| 5,171,574 A | 12/1992 | Kuberasampath et al. .. 424/423 |
| 5,324,819 A | 6/1994 | Oppermann et al. ........ 530/350 |
| 5,344,654 A | 9/1994 | Rueger et al. ............... 424/423 |
| 5,354,557 A | 10/1994 | Oppermann et al. ........ 424/423 |
| 5,459,047 A | 10/1995 | Wozney et al. ............. 435/69.1 |

FOREIGN PATENT DOCUMENTS

| WO | WO91/18558 | 12/1991 |
| WO | WO95/05846 | 3/1995 |
| WO | WO95/16035 | 6/1995 |
| WO | WO97/05241 | 2/1997 |
| WO | WO97/05285 | 2/1997 |
| WO | WO98/26069 | 6/1998 |

OTHER PUBLICATIONS

Canalis et al., Isolation and Characterization of Insulin–Like Growth Factor I (Somatomedin–C) from Cultures of Fetal Rat Calvariae, *Endocrinology*, 122, pp. 22–27 (1988).

Canalis et al., Skeletal Growth Factors Regulate the Synthesis of Insulin–Like Growth Factor Binding Protein–5 in Bone Cell Cultures, *J. Biol. Chem.*, 270, pp. 10771–10776 (1995).

Dong et al., Insulin–Like Growth Factor (IGF) I and Retinoic Acid Induce the Synthesis of IGF–Binding Protein 5 in Rat Osteoblastic Cells, *Endocrinology*, 136, pp. 2000–2006 (1995).

Gabbitas et al., Cortisol Inhibits the Synthesis of Insulin–Like Growth Factor–Binding Protein–5 in Bone Cell Cultures by Transcriptional Mechanisms, *J. Biol. Chem.*, 271, pp. 9033–9038 (1996).

Hock et al., Insulin–Like Growth Factor I Has Independent Effects on Bone Matrix Formation and Cell Replication, *Endocrinology*, 122, pp. 254–260 (1988).

(List continued on next page.)

Primary Examiner—Jezia Riley
(74) Attorney, Agent, or Firm—Fish & Neave; James F. Haley, Jr.; Karen Mangasarian

(57) ABSTRACT

The present invention relates generally to methods and compositions for identifying morphogenic protein analogs. In one embodiment, this invention relates to an osteogenic protein reponsive transcription inhibitory element. This invention also relates to the identified morphogenic protein analogs which can mimic the biological effects of morphogenic proteins, particularly those relating to the BMP family such as osteogenic protein (OP-1), on the regulation of gene expression and tissue inductive capabilities.

14 Claims, 13 Drawing Sheets

OTHER PUBLICATIONS

Ji, et al., Activation of the Insulin–Like Growth Factor–Binding Protein–5 Promoter in Osteoblasts by Cooperative E Box, CCAAT Enhancer–Binding Protein, and Nuclear Factor–1 Deoxyribonucleic Acid–Binding Sequences, *Endocrinology*, 140, pp. 4564–4572 (1999).

Liem et al., Dorsal Differentiation of Neural Plate Cells Induced by BMP–Mediated Signals from Epidermal Ectoderm, *Cell*, 82, pp. 969–979 (1995).

McCarthy et al., Regulatory Effects of Insulin–Like Growth Factors I and II on Bone Collagen Synthesis in Rat Calvarial Cultures, *Endocrinology*, 124, pp. 301–309 (1989).

Pash et al., Transcriptional Regulation of Insulin–Like Growth Factor–Binding Protein–5 by Prostaglandin $E_2$ in Osteoblast Cells, *Endocrinology*, 137, pp. 2375–2382 (1996).

Reddi, Cell Biology and Chemistry of Endochondral Bone Development, *Collagen Rel. Res.*, 1, pp. 209–226 (1981).

Sampath and Reddi, Dissociative Extraction and Reconstitution of Extracellular Matrix Components Involved in Local Bone Differentiation, *Proc. Natl. Acad. Sci. USA*, 78, pp. 7599–7603 (1981).

Sampath and Reddi, Homology of Bone–Inductive Proteins From Human, Monkey, Bovine, and Rat Extracellular Matrix, *Proc. Natl. Acad. Sci. USA*, 80, pp. 6591–6595 (1983).

Yeh et al., Osteogenic Protein–1–Mediated Insulin–Like Growth Factor Gene Expression in Primary Cultures of Rat Osteoblastic Cells, *Endocrinology*, 137, pp. 1921–1931 (1996).

Yeh et al., Osteogenic Protein–1and Insulin–Like Growth Factor I Synergistically Stimulate Rat Osteoblastic Cell Differentiation and Proliferation, *Endocrinology*, 138, pp. 4181–4190 (1997).

Yeh et al., Osteogenic Protein–1 Regulates Insulin–Like Growth Factor–I (IGF–I), IGF–II, and IGF–Binding Protein–5 (IGFBP–5) Gene Expression in Fetal Rat Calvaria Cells by Different Mechanisms, *J. Cell Physiol.*, 175, pp. 78–88 (1998).

Untreated Cell
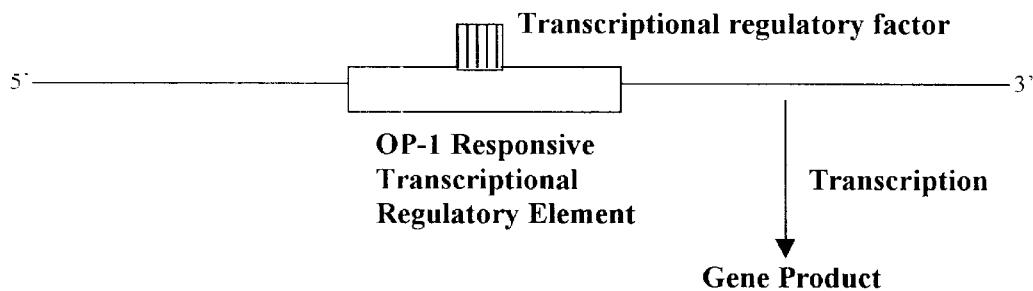
OP-1-treated Cell
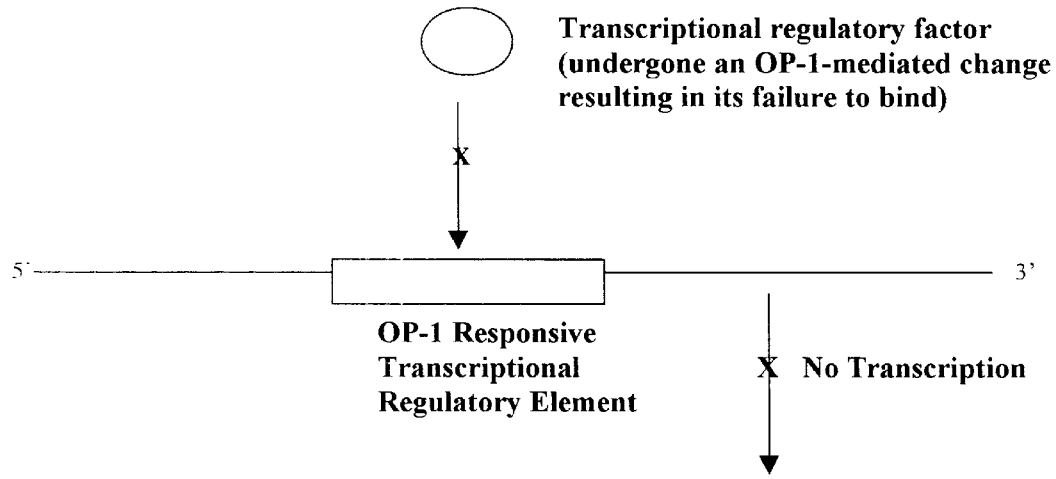
Figure 1

Figure 2

Rat IGFBP-5 Promoter Region (-888 to +114, +1 is the transcription start site)

```
-888        CTACCTTC CTTCCATTTA AAAGGACATT GAAGGTGTCT ATGTCACCAG ATAAAATTGA CCACCCACAG
-820 CATTTTCTCC AGGGACTCAG TCACTGCTCC CAACAAAGCT GGGGCAGAAG GGGGGGGTTA TCCTTTCTTG AAAGTACACA
-740 GTGCACACAC ACACACACAC ACACACACAC GTATCCCACC AGTCATCTAT GTAGGTGAAA
-660 GAAAATGACC ATTGAGTATA ACCAAAATCA GTATCCCACC AGAACAACAA CGACAAGCCC GTGCCATAAT CCCTCTGTCC
-580 GGACTTCTGA TGGGGGAGG GGTGTGTGTG CACACACACC AAACACACAG CCTTTAAATT CATCTCAACG CCCCTCACCA
-500 GCTACTGTAC ACTACTTGTC CCCAAACAC ACAGCAAAAC CTTCAATAGT CATTTAGACA CTTTTTTTTC
-420 TTAAGTTGGA AATGACTTCT TGGGTAGGGT ATACACGGCT AATAAGAAAA TGTGACTCCT AACAGCCAGT GTCCGGGCTA
-340 GTTGTCCAGA AAACCCACTC GCCCCATTGT GTTCACCCAG CTCCTGACGA TTACAGCCAT CCACCCCTCC CTCTACTTTC
-260 TCCCTCTTCT CCTCTGTAGC TCGCCCCGTA CCCCCAAGCC CTTTCCGTAC ATTCCGTGGG GAGGAGGGCG CTGTGCAGGG
-180 AGCGAAGGGG AGCCCCCGTG TCTAGAAGGC CTCTCCCCAC CCCCACCCCG TGTGAGTTTG CGCTGCAAAG CTCCCTGGCA
-100 TCCTTGCATG GGTTGGGTGT TGGGGAGCTC AAATTGCAGC TACAACTGGC TGGCAGCCAG GGGCCGTCTA TTTAAAAGCG
-20  CCTGCTCGAC CAGAGCCCGC AGTCTCTTTG GAAACTTCTG CCGGGGGTTT TAAAAGAGCT AGGAAAGAGC TGCAAAGCTG
+61  TTTGGGCTTT TTTTCCCCCC TTTTTGTTA CTTTTTGTTC TCCCCCTCCT CGGT
                                                                              +114
```

Alignment of IGFBP-5 partial promoter sequences

```
HUMAN   -82                                                                                        -21
        AGTTGGGTGT TGGGAAGCTC AAATTGCAGC TACAAACTGGC TGGCAGCCAG GGGCCGGCTA TTTAAAAGCG CCTGC

MOUSE   -79                                                                                        -19
        GGTTGGGTGT TGGGGAGCTC AAATTGCAGC TACAAACTGGC TGGCAGCCAG GGGCCGTCTA TTTAAAAGCG CCTGC

RAT     -80                                                                                        -20
        GGTTGGGTGT TGGGGAGCTC AAATTGCAGC TACAACTGGC  TGGCAGCCAG GGGCCGTCTA TTTAAAAGCG CCTGC
                  CAAT-box              E-box/c-Myb                        TATA box
                             C/EBPα
                                         BandShift probe
```

Figure 5A

Internal mutants

METHODS AND COMPOSITIONS FOR IDENTIFYING MORPHOGENIC PROTEIN ANALOGS USING MORPHOGENIC PROTEIN RESPONSIVE INHIBITORY ELEMENTS

FIELD OF THE INVENTION

The present invention relates generally to methods and compositions for identifying morphogenic protein analogs. In one embodiment, this invention relates to an osteogenic protein reponsive transcription inhibitory element. This invention also relates to the identified morphogenic protein analogs which can mimic the biological effects of morphogenic proteins, particularly those relating to the BMP family such as osteogenic protein (OP-1), on the regulation of gene expression and tissue inductive capabilities.

BACKGROUND OF THE INVENTION

Osteogenic proteins were defined originally as an activity present in mammalian bone extracts, presumably active during growth and natural bone healing, capable of inducing a developmental cascade leading to cartilage and endochondral bone accumulation when implanted in vivo. This developmental cascade includes mesenchymal cell recruitment and proliferation, progenitor cell differentiation, cartilage calcification, vascular invasion, bone formation, remodeling and marrow differentiation (Reddi, *Collagen Rel. Res.*, 1, pp. 209–26 (1981)).

The factors in bone matrix that induce endochondral bone differentiation can be dissociatively extracted and reconstituted with inactive collagenous matrix to restore full bone inductive activity (Reddi, *Proc. Natl. Acad. Sci. USA*, 78, pp. 7599–7603 (1981)). This provides an experimental method for assaying protein extracts for their ability to induce endochondral bone formation in vivo. Using this reconstitution assay, a variety of related osteogenic proteins have been isolated from several mammalian species that are capable of inducing bone and cartilage formation in cross-species implants (Sampath and Reddi, *Proc. Natl. Acad. Sci. USA*, 80, pp. 6591–95 (1983)). The active factor or factors that promote this activity have been referred to in the literature most commonly as bone morphogenetic proteins (BMPs) and osteogenic proteins (OPs).

Osteogenic and bone morphogenetic proteins represent a family of structurally and functionally related morphogenic proteins belonging to the Transforming Growth Factor-Beta (TGF-β) superfamily (see below). The TGF-β superfamily, in turn, represents a large number of evolutionarily conserved proteins with diverse activities involved in growth, differentiation and tissue morphogenesis and repair. BMPs and osteogenic proteins, as members of the TGF-β superfamily, are expressed as secretory polypeptide precursors which share a highly conserved bioactive cysteine domain located near their C-termini. Another feature of many of the BMP family proteins is their propensity to form homo- and heterodimers.

Many morphogenic proteins belonging to the BMP family have now been described. Some have been isolated using purification techniques coupled with bioassays such as the one described above. Others have been identified and cloned by virtue of DNA sequence homologies within conserved regions that are common to the BMP family. These homologs are referred to as consecutively-numbered BMPs whether or not they have demonstrable osteogenic activity. Using an alternative approach, synthetic OPs having osteogenic activity have been designed using amino acid consensus sequences derived from sequence comparisons between naturally-derived OPs and BMPs (see below; Oppermann et al., U.S. Pat. No. 5,324,819).

While several of the earliest members of the BMP family were osteogenic proteins identified by virtue of their ability to induce new cartilage and bone, the search for BMP-related genes and gene products in a variety of species has revealed new morphogenic proteins, some of which have different or additional tissue-inductive capabilities. For example, BMP-12 and BMP-13 (identified by DNA sequence homology) reportedly induce tendon/ligament-like tissue formation in vivo (WO 95/16035). Several BMPs can induce neuronal cell proliferation and promote axon regeneration (WO 95/05846). And some BMPs that were originally isolated on the basis of their osteogenic activity also have neural inductive properties (Liem et al., *Cell*, 82, pp. 969–79 (1995)). It thus appears that osteogenic proteins and other BMPs may have a variety of potential tissue inductive capabilities whose final expression may depend on a complex set of developmental and environmental cues. These osteogenic, BMP and BMP-related proteins are referred to herein collectively as morphogenic proteins.

Moreover, osteogenic proteins can stimulate the synthesis of several growth factors, such as the insulin-like growth factors (IGFs) in cultured osteoblastic cells. IGF-I and IGF-II exhibit mitogenic activity in bone cells and enhance osteoblast differentiation (Hock et al., *Endocrinology*, 122, pp. 254–260 (1988); McCarthy et al., *Endocrinology*, 124, pp. 301–309 (1989); Yeh et al., *Endocrinology*, 137, pp. 1921–1931 (1996)). The biological activity of the IGFs can be affected by their binding proteins, the insulin-like growth factor binding proteins (IGFBP). The IGFBPs have differential activities on bone formation and can be differentially regulated by various factors, including osteogenic proteins, cortisol, prostaglandin E2, basic fibroblast growth factor (bFGF), platelet-derived growth factor (PDGF), and TGF-β (Canalis et al., *J. Biol. Chem.*, 270, pp. 10771–10776 (1995); Dong et al., *Endocrinology*, 136, 2000–2006 (1995); Yeh et al., *J. Cell Physiol.*, 175, 78–88 (1998); Pash et al., *Endocrinology*, 137, 2375–2382 (1996); Canalis et al., *Endocrinology*, 122, 22–27 (1988); Gabbitas et al., *J. Biol. Chem.*, 271, 9033–9038 (1996).

The activities described above, and other as yet undiscovered tissue inductive properties of the morphogenic proteins belonging to the BMP family are expected to be useful for promoting tissue regeneration in patients with traumas caused, for example, by injuries or degenerative disorders. Implantable osteogenic devices comprising mammalian osteogenic protein for promoting bone healing and regeneration have been described (see, e.g., Oppermann et al., U.S. Pat. No. 5,354,557). Some osteogenic devices comprise osteogenic protein dispersed in porous, biocompatible matrices. These naturally-derived or synthetic matrices typically allow osteogenic protein to diffuse out of the matrix into the implantation site and permit influx and efflux of cells. Osteogenic protein induces the progenitor cells to differentiate and proliferate. Progenitor cells may migrate into the matrix and differentiated cells can move out of the porous matrix into the implant site. Osteogenic cells may also utilize the matrix as a physical scaffold for osteoconduction. Similar devices have been described for delivering BMPs for tendon/ligament-like and neural tissue regeneration (see below). Osteogenic protein-coated prosthetic devices which enhance the bond strength between the prosthesis and existing bone have also been described (Rueger et al., U.S. Pat. No. 5,344,654, incorporated herein by reference).

The availability of large amounts of purified and highly active morphogenic proteins would revolutionize orthopedic medicine, certain types of plastic surgery, dental and various periodontal and craniofacial reconstructive procedures, and procedures generally involving bone, cartilage, tendon, ligament and neural regeneration. Many of the mammalian OP- and BMP-encoding genes are now cloned and may be recombinantly expressed as active homo- and heterodimeric proteins in a variety of host systems, including bacteria. The ability to produce morphogenic protein analogs, including variants and mutants with increased bioactivities (see below), make potential therapeutic treatments using morphogenic protein analogs feasible.

Given the large number of potential therapeutic uses for morphogenic proteins in treating a variety of different tissues and tissue-types, there is a need for identifying therapeutically effective analogs of these morphogenic proteins. It would thus be desirable to identify and produce analogs that are inexpensive, have a long shelf-life, and have increased tissue inductive activity and few side effects. Treatment with a morphogenic protein analog having increased tissue inductive activity, could induce tissue formation more rapidly, or in a tissue-specific manner.

SUMMARY OF THE INVENTION

The present invention solves these problems by providing methods and compositions for identifying morphogenic protein analogs. Compounds identified according to methods set forth herein are provided. This invention also provides methods for producing commercially useful quantities of the identified morphogenic protein analog. Methods for the preparation and use of a DNA sequence comprising a morphogenic protein responsive transcription inhibitory element are also provided. The DNA of this invention can be used to suppress the expression of a gene of interest. Further, the DNA of the present invention can be used in the preparation of a cell for the in vivo or in vitro inhibtion of a detectable product which is inducible by the compounds of this invention. This invention provides pharmaceutical compositions comprising a morphogenic protein analog. Implantable morphogenic devices, comprising a morphogenic protein analog capable of inducing tissue formation in allogenic and xenogenic implants are also provided.

Other features and advantages of the invention will be apparent from the following detailed description, and from the claims.

BRIEF DESCRIPTION OF THE DRAWINGS

FIG. 1. A schematic representation illustrating the action of OP-1 on the OP-1 responsive transcriptional regulatory element. Treatment with OP-1 mediates a change in the OP-1 transcription regulatory factor resulting in the failure of the OP-1 transcription regulatory factor to bind to the OP-1 responsive transcriptional regulatory element. The lack of binding results in inhibition of transcription of the gene operably linked with the OP-1 responsive transcriptional regulatory element.

FIG. 2. DNA sequence of a region (−888 to +114) of the rat IGFBP-5 promoter and partial coding sequence.

DETAILED DESCRIPTION OF THE INVENTION

Figure 3:
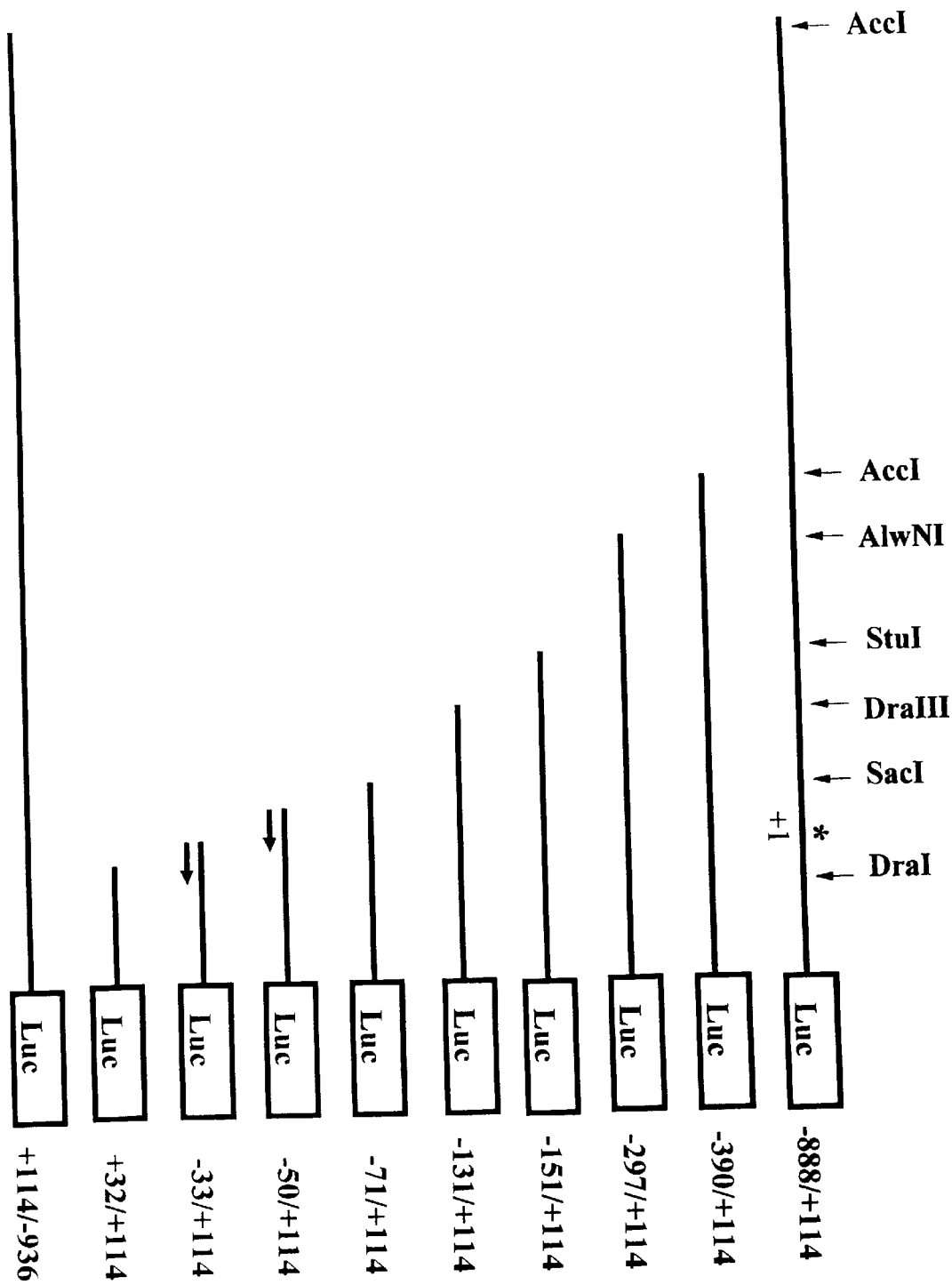
FIG. 3. DNA constructs containing different rat IGFBP-5 promoter regions. The transcription start site is +1. The DNA fragment was subcloned into the pGL2-Basic vector containing the luciferase reporter gene (Luc). The 5' deletion fragments were generated by digestion of the parent DNA with unique restriction enzymes or PCR as indicated. The unique restriction sites are shown (perpendicular arrows). Positions of primers used for PCR are indicated as horizontal arrows.

In order that the invention herein described may be fully understood, the following detailed description is set forth.

The term "bone morphogenetic protein (BMP)" refers to a protein belonging to the BMP family of the TGF-β superfamily of proteins (BMP family) based on DNA and amino acid sequence homology. A protein belongs to the BMP family according to this invention when it has at least 50% amino acid sequence identity with at least one known BMP family member within the conserved C-terminal cysteine-rich domain which characterizes the BMP protein family. Members of the BMP family may have less than 50% DNA or amino acid sequence identity overall.

The term "morphogenic protein" refers to a protein having morphogenic activity (see below). Preferably a morphogenic protein of this invention comprises at least one polypeptide belonging to the BMP protein family. Morphogenic proteins may be capable of inducing progenitor cells to proliferate and/or to initiate differentiation pathways that lead to cartilage, bone, tendon, ligament, neural or other types of tissue formation depending on local environmental cues, and thus morphogenic proteins may behave differently in different surroundings. For example, an osteogenic protein may induce bone tissue at one treatment site and neural tissue at a different treatment site.

The term "osteogenic protein (OP)" refers to a morphogenic protein that is capable of inducing a progenitor cell to form cartilage and/or bone. The bone may be intramembranous bone or endochondral bone. Most osteogenic proteins are members of the BMP protein family and are thus also BMPs. However, the converse may not be true. BMPs (identified by sequence homology) must have demonstrable osteogenic activity in a functional bioassay to be osteogenic proteins according to this invention.

The term "OP-1 responsive cell" refers to any cell that displays a receptor on its cell surface that is capable of binding to OP-1 and inducing an OP-1-mediated biological effect. The cell surface receptor may be endogenously expressed or expressed as a result of transfecting the DNA encoding the receptor into the target cell.

The term "morphogenic protein responsive cell" refers to any cell that displays a receptor on its cell surface that is capable of binding to a morphogenic protein and inducing a morphogenic protein-mediated biological effect. The cell surface receptor may be endogenously expressed or expressed as a result of transfecting the DNA encoding the receptor into the target cell.

The terms "morphogenic activity", "inducing activity", "tissue inductive activity", "morphogenic protein mediated biological effect" and "biological effect mediated by a morphogenic protein" alternatively refer to the ability of an agent to stimulate a target cell to undergo one or more cell divisions (proliferation) that may optionally lead to cell differentiation. Such target cells are referred to generically herein as progenitor cells. Cell proliferation is typically characterized by changes in cell cycle regulation and may be detected by a number of means which include measuring DNA synthetic or cellular growth rates. Early stages of cell differentiation are typically characterized by changes in gene expression patterns relative to those of the progenitor cell, which may be indicative of a commitment towards a particular cell fate or cell type. Later stages of cell differentiation may be characterized by changes in gene expression patterns, cell physiology and morphology. Any reproducible change in gene expression, cell physiology or morphology may be used to assess the initiation and extent of cell differentiation induced by a morphogenic protein.

The term "morphogenic protein analog" is a substance that can mimic the biological effects, including morphogenic activity, inducing activity and tissue inductive activity, that are characteristic of a morphogenic protein such as osteogenic protein.

Morphogenic Responsive Transcription Regulatory Element

This invention is based on the discovery that morphogenic proteins, including OP-1, can regulate gene expression in mammals. The stimulation of mammalian cells with osteogenic protein induces a wide array of biological activities and regulates the expression of numerous cellular genes. The promoter region of at least one such gene has been analyzed and found to contain an osteogenic protein responsive transcription inhibitory element.

The present invention exploits the OP-1 responsive properties of the transcription inhibitory element of the insulin-like growth factor binding protein-5 (IGFBP-5) gene. FIG. 1 is a schematic illustration of the action of OP-1 on the OP-1 responsive transcriptional regulatory element. FIG. 1 demonstrates that the present OP-1 responsive transcription inhibitory element is present within an OP-1 responsive cell. In the absence of OP-1, the transcription regulatory factor interacts with the OP-1 responsive transcriptional regulatory element located within the promoter region which is operably linked with a downstream gene resulting in transcription of that gene. Upon contact of OP-1 with the OP-1 responsive cell, the transcription regulatory factor undergoes an OP-1 mediated change resulting in its failure to bind to the OP-1 responsive transcription inhibitory element. This lack of binding inhibits or down regulates the transcription of genes operably linked and located downstream of the element.

In a preferred embodiment, the transcription regulatory factor interacts with the OP-1 responsive transcription inhibitory element located within the promoter region of the insulin-like growth factor binding protein-5 (IGFBP-5), at a 21 bp region which contains sequences resembling the C/EBPα-like element, c-Myb motif and E-box-like motif. Mutation and deletion analysis of this OP-1 responsive transcription inhibitory element results in a loss of OP-1 responsive transcription inhibition of downstream elements that are operably linked with the element (See FIGS. 4 and 6).

The methods and compositions of this invention utilize the OP-1 responsive properties of osteogenic protein transcription inhibitory elements to identify morphogenic protein analogs. In one embodiment of this invention, the OP-1 responsive transcription inhibitory element located in the promoter region of the rat IGFBP-5 gene is used to identify morphogenic protein analogs that can mimic the biological effects induced by a morphogenic protein such as OP-1.

Thus, in view of this disclosure, the skilled practitioner can identify and evaluate novel morphogenic protein analogs, thereby increasing the number of potential therapeutic compounds for use in treatment of injuries and diseases for which morphogenic proteins are considered to be clinically useful.

Morphogenic Proteins

The morphogenic proteins of this invention are capable of stimulating a progenitor cell to undergo a cascade of biological events culminating in cell division and differentiation. Many mammalian morphogenic proteins have been described. Some fall within a class of products called "homeodomain proteins", named for their homology to the drosophila homeobox genes involved in phenotypic expression and identity of body segments during embryogenesis. Other morphogenic proteins are classified as peptide growth factors, which have effects on cell proliferation, cell differentiation, or both.

Peptide growth factors may be grouped into a number of superfamilies or families based primarily on their sequence similarity (Mercola and Stiles, *Development*, 102, pp. 461–60 (1988)). These families include: Epidermal Growth Factor (e.g., EGF, TGF-α, notch and delta), Transforming Growth Factor-Beta (e.g., TGF-β, inhibin, activin, MIS, BMP, dpp and Vg-1); Heparin Binding Growth Factor (e.g., FGF, ECDGF and int-2); Platelet Derived Growth Factor; Insulin-like Growth Factor (IGF-I, IGF-II); and Nerve Growth Factor.

The BMP Family

The morphogenic proteins of this invention preferably belong to the TGF-β protein superfamily. Members of the TGF-β superfamily are divided further into families based on their degree of structural or functional similarity. The BMP family is one such family, named for its representative bone morphogenetic/osteogenic protein family members. Of the reported "BMPs" (BMP-1 to BMP-18), isolated primarily based on sequence homology, all but BMP-1 remain classified as members of the BMP family of morphogenic proteins (Ozkaynak et al., *EMBO J.*, 9, pp. 2085–93 (1990)).

The BMP family includes other structurally-related members which are morphogenic proteins, including the drosophila decapentaplegic gene complex (DPP) products, the Vg1 product of *Xenopus laevis* and its murine homolog, Vgr-1 (see, e.g., Massagué, J., "The Transforming Growth Factor-β Family", *Annu. Rev. Cell Biol.*, 6, pp. 597–641 (1990)).

A morphogenic protein according to this invention belongs to the BMP family when it comprises a polypeptide having at least 50% amino acid sequence identity with at least one known BMP family member, within the conserved C-terminal cysteine-rich domain which characterizes the BMP protein family. This definition is in part derived from comparing amino acid sequence identities between C-terminal domains of other BMP family members that have demonstrable morphogenic activity.

The Drosophila DPP and Xenopus Vg-1 gene products are 50% identical to each other (and 35–40% identical to TGF-β). Both the Dpp and Vg-1 products are morphogenic proteins that participate in early patterning events during embryogenesis of their respective hosts. These products appear to be most closely related to mammalian bone morphogenetic proteins BMP-2 and BMP-4, whose C-terminal domains are 75% identical with that of Dpp.

The C-terminal domains of BMP-3, BMP-5, BMP-6, and OP-1 (BMP-7) are about 60% identical to that of BMP-2, and the C-terminal domains of BMP-6 and OP-1 are 87% identical. BMP-6 is likely the human homolog of the murine Vgr-1 (Lyons et al., *Proc. Natl. Acad. Sci. U.S.A.*, 86, pp. 4554–59 (1989)); the two proteins are 92% identical overall at the amino acid sequence level (U.S. Pat. No. 5,459,047, incorporated herein by reference). BMP-6 is 58% identical to the Xenopus Vg-1 product.

The DNA and amino acid sequences of these and other BMP family members are published and may be used by those of skill in the art to determine whether a candidate morphogenic protein analog belongs to the BMP family. New BMP-related gene products are expected by analogy to possess at least one morphogenic activity and thus classified as a morphogenic protein analog.

Another characteristic of the BMP protein family members is their apparent ability to dimerize. Several bone-derived osteogenic proteins (OPs) and BMPs are found as homo- and heterodimers in their active forms. The ability of OPs and BMPs to form heterodimers may confer additional or altered morphogenic inductive capabilities on morphogenic proteins. Heterodimers may exhibit qualitatively or quantitatively different binding affinities than homodimers for OP and BMP receptor molecules. Altered binding affinities may in turn lead to differential activation of receptors that mediate different signalling pathways, which may ultimately lead to different biological activities or outcomes. Altered binding affinities could also be manifested in a tissue or cell type-specific manner, thereby inducing only particular progenitor cell types to undergo proliferation and/or differentiation.

Suitable in vitro, ex vivo and in vivo bioassays known in the art, including those described herein, may be used to ascertain whether a new BMP-related gene product or a new heteromeric species has a known or a new morphogenic activity. Expression and localization studies defining where and when the gene and its product(s) are expressed may also be used to identify potential morphogenic activities. Nucleic acid and protein localization procedures are well known to those of skill in the art (see, e.g., Ausubel et al., eds. *Current Protocols in Molecular Cloning*, Greene Publishing and Wiley Interscience, New York, 1989).

Many of the identified BMPs are osteogenic and can induce bone and cartilage formation when implanted into mammals. Some BMPs identified based on sequence homology to osteogenic proteins possess other morphogenic activities. For example, BMP-12 and BMP-13 reportedly induce ectopic formation of tendon/ligament-like tissue when implanted into mammals (Celeste et al., WO 95/16035). Using this bioassay, or any other suitable assay selected by the skilled practitioner, one or more morphogenic proteins that are capable of inducing tendon/ligament-like tissue formation can be identified and optimized according to the procedures described herein.

Certain BMPs which are known to be osteogenic can also induce neuronal cell differentiation. Embryonic mouse cells treated with BMP-2 or OP-1 (BMP-7) differentiate into astrocyte-like (glial) cells, and peripheral nerve regeneration using BMP-2 has been recently reported (Wang et al., WO 95/05846). In addition, BMP-4, BMP-5 and OP-1 (BMP-7) are expressed in epidermal ectoderm flanking the neural plate. Ectopic recombinant BMP-4 and OP-1 (BMP-7) proteins are capable of inducing neural plate cells to initiate dorsal neural cell fate differentiation (Liem et al., *Cell*, 82, pp. 969–79 (1995)). At the spinal cord level, OP-1 and other BMPs can induce neural crest cell differentiation. It is suggested that OP-1 and these BMPs can induce many or all dorsal neural cell types, including roof plate cells, neural crest cells, and commissural neurons, depending on localized positional cues.

That several osteogenic proteins originally derived from bone matrix appear to be localized to embryonic nervous system and to have neurogenic inductive properties makes it likely that these and other members of the BMP protein family will have additional tissue inductive properties that are not yet disclosed. It is envisioned that the ability to mimic tissue inductive properties of morphogenic proteins using a morphogenic protein analog as set forth herein will be useful for mimicking the new tissue inductive properties of known morphogenic proteins.

Production of Morphogenic Proteins

The morphogenic proteins of this invention may be derived from a variety of sources. Morphogenic proteins may be isolated from natural sources, or may be produced by expressing an appropriate recombinant DNA molecule in a host cell. In addition, the morphogenic proteins of this invention may be derived synthetically and synthetic morphogenic proteins may optionally be expressed from a recombinant DNA molecule in a host cell.

Preferred Morphogenic Proteins

In one embodiment of this invention, the morphogenic protein whose activity is mimicked by a morphogenic protein analog comprises a pair of subunits disulfide bonded to produce a dimeric species, wherein at least one of the subunits comprises a recombinant polypeptide belonging to the BMP protein family. The dimeric species may be a homodimer or heterodimer and is capable of inducing cell proliferation and/or tissue formation when accessible to a progenitor cell in the mammal. The progenitor cell may be induced to form one or more tissue types preferably selected from the group consisting of endochondral or intramembranous bone, cartilage, tendon/ligament-like tissue neural tissue and other organ tissue types, including kidney tissue. In another preferred embodiment, the morphogenic protein is an osteogenic protein that is capable of inducing the progenitor cell to form one or more tissue types selected from the group consisting of endochondral or intramembranous bone and cartilage.

Preferred morphogenic and osteogenic proteins of this invention comprise at least one polypeptide selected from the group consisting of BMP-2, BMP-4, BMP-5, BMP-6, OP-1 (BMP-7), BMP-8, BMP-9, BMP-10, BMP-11, BMP-12, BMP-13, BMP-14, BMP-15, BMP-16, BMP-17, BMP-18, COP-5 and COP-7. Preferably, the morphogenic protein comprises at least one polypeptide selected from the group consisting of OP-1 (BMP-7), BMP-2, BMP-4, BMP-5 and BMP-6; more preferably, OP-1 (BMP-7)and BMP-2; and most preferably, OP-1 (BMP-7).

As the skilled practitioner will appreciate, the preferred morphogenic protein whose activity is mimicked by a morphogenic protein analog of this invention will depend in part on the tissue type to be generated and on the selected implantation or treatment site. These variables may be tested empirically.

Morphogenic Protein Analogs

A morphogenic protein analog according to this invention is a compound that is capable of mimicking at least one biological effect that is induced or mediated by a morphogenic protein in a target cell or tissue. In one embodiment, the target cell or tissue is a morphogenic protein responsive cell or tissue. This morphogenic protein responsive cell or tissue can be endogenously responsive to the morphogenic protein or as a result of transfection into the cell the DNA encoding a receptor capable of binding to the morphogenic protein. Morphogenic protein mediated effects include the cellular and molecular responses, such as the induction of tissue formation from a progenitor cell, resulting from exposure of cells or tissues to morphogenic proteins.

The progenitor cell that is induced to proliferate and/or differentiate by the morphogenic protein of this invention is preferably a mammalian cell. Preferred progenitor cells include mammalian chondroblasts, osteoblasts and neuroblasts, all earlier developmental precursors thereof, and all cells that develop therefrom (e.g., chondroblasts, pre-chondroblasts and chondrocytes). However, morphogenic proteins are highly conserved throughout evolution, and non-mammalian progenitor cells are also likely to be stimulated by same- or cross-species morphogenic proteins and morphogenic protein analogs. It is thus envisioned that when schemes become available for implanting xenogenic cells into humans without causing adverse immunological reactions, non-mammalian progenitor cells stimulated by morphogenic proteins analogs according to the procedures set forth herein will be useful for tissue regeneration and repair in humans.

In a preferred embodiment the morphogenic protein mediated biological effect is an OP-1 mediated biological effect.

An OP-1 mediated biological effect is any biological effect resulting from the contact of an OP-1 responsive cell or tissue with OP-1, either in vivo or in vitro. Biological effects specifically mediated by OP-1, include those effects that are associated with the induction of proliferation and differentiation of chondroblasts, osteoblasts and neuroblasts, all earlier developmental precursors thereof, and all cells that develop therefrom (e.g., chondroblasts, pre-chondroblasts and chondrocytes). The biological effects may be biochemical or molecular. A preferred biological effect of this invention is the inhibition of gene expression and the failure of a transcription regulatory factor to bind to the OP-1 responsive transcription inhibitory element.

Specific OP-1 mediated biological effects associated with endochondral bone formation include the induction of cell proliferation or mitogenesis, induction of phenotypic markers of differentiation, regulation of gene expression. In a preferred embodiment, the OP-1 mediated effect is the inhibition or down regulation of gene expression.

Identifying Putative Morphogenic Protein Analogs

In one embodiment of this invention, a method for identifying a compound capable of inducing a morphogenic protein mediated biological effect is provided. The method involves the steps of a) providing a target cell comprising a DNA sequence comprising a morphogenic protein responsive transcription inhibitory element operably linked to a reporter gene or genes encoding a detectable product, wherein the DNA sequence, when present in a morphogenic protein responsive cell exposed to a morphogenic protein, down-regulates transcription of the the gene or genes it controls; b) exposing the target cell to a test compound; and c)comparing the level of production of the detectable product, with the level observed in the absence of the test compound. The present morphogenic protein (OP-1) responsive transcription inhibitory element is a cis-acting element that regulates the expression of a gene located downstream of the regulatory element in a morphogenic protein responsive cell. In a preferred embodiment, the cis-acting element us the OP-1 responsive transcription inhibitory element from the rat IGFBP-5 promoter.

The OP-1 responsive transcription inhibitory element of this invention may be located between about 25 base pairs and 3 kilobase pairs upstream of the gene transcription initiation site. In one embodiment the OP-1 responsive transcription inhibitory element is located between about 25 base pairs and 2 kilobase pairs upstream of the gene transcription initiation site. In another embodiment the OP-1 responsive transcription inhibitory element is located between about 25 base pairs and 1 kilobase pair upstream of the gene transcription initiation site. In a preferred embodiment, the OP-1 responsive transcription inhibitory element is located between about 25–500 base pairs upstream of the gene transcription initiation site. In a more preferred embodiment, the OP-1 responsive transcription inhibitory element is located between about 25–150 base pairs upstream of the transcription start site.

Accordingly, in one embodiment, the OP-1 responsive transcription inhibitory element comprises nucleotides 817–837 of SEQ ID NO. 1. In another embodiment, the OP-1 responsive transcription inhibitory element comprises nucleotides 807–847 of SEQ ID NO. 1. In yet another embodiment, the OP-1 responsive transcription inhibitory element comprises nucleotides 799–857 of SEQ ID NO. 1.

In addition, the OP-1 responsive transcription inhibitory element of this invention is operably linked to a downstream gene encoding a detectable product such that when OP-1 interacts with its cell surface receptor on an OP-1 responsive cell, an intracellular cascade of events is induced. One result of the induction of the intracellular cascade is the down regulation of transcription of a gene located downstream from and operably linked to the OP-1 responsive transcription inhibitory element.

The present target cell is any cell comprising a DNA sequence comprising the morphogeinc protein responsive transcription inhibitory element operably linked to a reporter gene encoding a detectable product. This DNA can either be naturally present in the target cell or be transfected into the target cell. The induced intracellular cascade of events that is characteristic of the morphogenic protein analogs includes a variety of intracellular signal transduction molecules (e.g., cyclic nucleotides, protein kinases, diacylglycerol, SMADs, protein phosphatases). These intracellular signal transduction molecules cause the regulation of gene expression, including modifications in transcription and/or translation.

The target cells of this invention are preferably mammalian cells and include but are not limited to osteogenic progenitor cells, calvarial cells, osteosarcoma cells, osteoblasts, osteoclasts, cartilage as well as neural cells. Any cell that is responsive to morphogenic proteins including OP-1, may be used for determining whether a test compound is a morphogenic protein analog. Moreover, the target cell may be naturally responsive due to endogenous expression of a morphogenic protein receptor capable of binding a morphogenic protein or morphogenic protein analog or as a result of transfection into the target cell the DNA encoding a receptor capable of binding to the morphogenic protein or morpogenic protein analog.

The method of identifying the morphogenic protein analog is by using a reporter gene system wherein the target cells are exposed to a test compound and the down-regulation of the expression of a detectable gene operably linked to the OP-1 responsive element of the present invention is measured. Down-regulation of this gene product indicates that the test compound can induce an OP-1 mediated biological effect and is therefore a morphogenic protein analog.

Several reporter genes useful for identifying morphogenic protein analogs are available. Specific details of the various technical aspects of these reporter systems are found in F. A. Ausubel, et al. Eds., *Current Protocols in Molecular Biology*, John Wiley & Sons, New York, (1989). Moreover, as will be appreciated by those of skill in the art, any gene that encodes a detectable product (RNA or protein) may be used as a reporter gene system for identifying a morphogenic protein analog. Accordingly, the detectable product in this invention may be RNA or protein.

In one embodiment of this invention, the reporter gene system is the firefly luciferase reporter system and the detectable product is luciferase. Using recombinant DNA techniques, various fusions of the IGFBP-5 promoter linked to the luciferase reporter gene were constructed (Example 2). This assay offers a sensitive, rapid, non-radioactive assay for measurement of promoter activity (Gould, S. J. et al. *Anal. Biochem.*, 7, 5–13 (1988); Brasier, A. R. et al., *Biotechniques*, 7, 1116–1122 (1989)). Target cells are lysed to release the reporter protein luciferase. The lysates are then combined with ATP and the substrate luciferin. The luciferase enzyme catalyzes a rapid ATP-dependent oxidation of the substrate, which then emits light. The total light output is measured and is proportional to the amount of luciferase present over a wide range of enzyme concentrations.

Another useful reporter system is the chloramphenicol acetyl transferase (CAT) system. Accordingly, in another embodiment the detectable product is chloramphenicol acetyl transferase. This system has been the most frequently used reporter system. Thus, a major advantage of this system is that it is an extensively validated and widely accepted measure of promoter activity. CAT is an enzyme that catalyzes the transfer of the acyl group from acetyl CoA to chloramphenicol. In this assay, target cells are lysed to release the CAT and the lysates are incubated with acteyl CoA and radioactively labeled chloramphenicol. The acetylated derivatives of chloramphenicol are separated from the non-acetylated forms using either thin-layer chromatography or a phase extraction. The degree of acetylation reflects the amount of CAT gene activity.

Yet another useful reporter system is the human growth hormone (hGH) reporter system which is immunologically based. This system is relatively quick and easy to use. hGH is assayed in the media, rather than in cell extracts. This allows monitoring of expression directed by a single population of transfected cells over time without destruction of the cells. Accordingly, in yet another embodiment the detectable product is hGH.

In order to determine whether a test compound is a morphogenic protein analog, prior to assaying the down-regulation of a particular gene as described above, the target cell is exposed to the test compound for a period of time and under cell culture conditions sufficient to induce an OP-1 mediated biological effect. Using the preferred OP-1 responsive transcription inhibitory element and fetal rat calvarial (FRC) cells, the OP-1-mediated biological effect is induced at least 24 hours (Example 3). In certain embodiments of this invention, the morphogenic protein-mediated biological effect is detected following at least 16–72 hours of exposure to a morphogenic protein analog. Preferably, the biological effect is detected following 24 hours of exposure to a morphogenic protein analog. As will be appreciated by the skilled practitioner, the determination of the precise cell culture conditions and time of culture can be ascertained by routine experimentation.

In one embodiment, the effectiveness of a test compound identified by the method of this invention can be confirmed by the step of exposing a morphogenic protein responsive cell to test compound and detecting biological effects that are mediated by a morphogenic protein. Accordingly the method of this invention further comprises the step of detecting the induction by the test compound of a biological effect mediated by a morphogenic protein. The biological effect is selected from the group of an alteration in binding of an intracellular molecule to the morphogenic protein responsive transcription inhibitory element, the induction of phenotypic markers of differentiation, the induction of a progenitor cell to form endochondral or intramembranous bone, the induction of a progenitor cell to form cartilage, or the induction of a progenitor cell to form tissue/ligament-like or neural like tissue. Preferably the biological effect mediated by a morphogenic protein is the induction of a progenitor cell to form one or more tissue types preferably selected from the group comprising endochondral or intramembranous bone, cartilage, tendon/ligament-like tissue, neural tissue and other organ tissue types, including kidney tissue. More preferably, the morphogenic protein is an osteogenic protein that is capable of inducing the progenitor cell to form one or more tissue types selected from the group consisting of endochondral or intramembranous bone and cartilage.

In another embodiment, the morphogenic protein responsive cell is an OP-1 responsive cell and the and the morphogenic protein mediated effect is an OP-1 mediated effect.

The biological effects include but are not limited to the induction of phenotypic markers associated with chondrocyte and osteoblast differentiation in fetal rat calvarial cells (e.g., alkaline phosphatase activity, bone nodule formation, osteocalcin expression). In addition, a biological effect includes alterations in the binding of intracellular molecules such as a transcription regulatory factors, to the OP-1 responsive transcription inhibitory element.

In yet another embodiment, the effectiveness of a test compound identified by the method of this invention can be confirmed by determining the binding of an intracellular molecule, such as a transcription regulatory factor, to the OP-1 responsive transcription inhibitory element.

The binding of an intracellular molecule to the OP-1 responsive element can be determined using gel mobility shift analysis (Example 4). This assay is based on the observation that DNA-protein complexes migrate through low-ionic strength polyacrylamide gels more slowly than unbound DNA fragments. This assay is a sensitive method for detecting sequence specific DNA-binding by proteins in cellular extracts. This assay also permits the quantitative determination of the affinity, abundance, association rate constants, dissociation rate constants and binding specificity of the DNA-binding proteins. Proteins that bind specifically to an end-labeled DNA fragment retard the mobility of the fragment during electrophoresis resulting in discrete bands corresponding to the individual protein-DNA complexes.

In a further embodiment the effectiveness of a test compound identified by the method of this invention can be confirmed by the step of exposing a tissue locus in a mammal to the morphogenic protein analog of this invention, and detecting the induced morphogenesis of the tissue. Accordingly, the method of this invention further comprises the step of exposing the test compound that induces a level of production of the detectable product that is less than the level observed in the absence of the test compound, to a tissue locus and detecting the ability of the morphogenic protein analog to induce tissue formation in a mammal.

OP-1 Transcription Inhibitory Element

In an embodiment of this invention, a DNA sequence for inducing an OP-1 mediated biological effect is provided. The DNA sequence comprises an OP-1 responsive transcription inhibitory element operably linked to a reporter gene such that, when present in an OP-1 responsive cell contacted with OP-1, the transcription of a reporter gene operably linked to said DNA sequence and located downstream of the element is down-regulated or inhibited. In one embodiment, the DNA sequence comprising the morphogenic protein responsive transcription inhibitory element comprises nucleotides 1–1002 of SEQ ID NO. 1 (−888−+114 in FIG. 2). In another embodiment, the morphogenic protein responsive transcription inhibitory element comprises nucleotides 498–1002 (−390−+114 in FIG. 2) of SEQ ID NO. 1. In yet another embodiment, the morphogenic protein responsive transcription inhibitory element comprises nucleotides 591–1002 (−297−+114 in FIG. 2) of SEQ ID NO. 1. In another embodiment, the morphogenic protein responsive transcription inhibitory element comprises nucleotides 732–1002 (−151−+114) of SEQ ID NO. 1. In yet another embodiment, the morphogenic protein responsive transcription inhibitory element comprises nucleotides 757–1002 (−131−+114) of SEQ ID NO. 1. In a preferred embodiment, the morphogenic protein responsive transcription inhibitory element comprises nucleotides 807–847 (−81−−41) of SEQ ID NO. 1. In a most preferred embodiment, the morphogenic protein responsive transcription inhibitory element comprises nucleotides 817–837 (−71−−51) of SEQ ID NO. 1.

Thus, a preferred morphogenic protein responsive transcription inhibitory element comprises nucleotides 817–837 (−71−−51) of SEQ ID NO. 1. This DNA sequence comprises the nucleotides sequences known as the CAAT-like sequence (nucleotides 1–5 of SEQ ID NO. 6), C/EBPα-like element (nucleotides 5–15 of SEQ ID NO. 6), and a c-myb or E-box-like motif (nucleotides 14–20 of SEQ ID NO. 6). Each of these sequences is capable of binding to its respective DNA binding protein. Thus, the CAAT-like sequence binds a CAAT binding protein, the C/EBPα-like element binds C/EBPα, the c-myb motif binds c-myb and the E-box-like motif binds the E-box binding protein. Mutation within this 21 base pair nucleotide sequence (nucleotides 1–21 of SEQ ID NO. 6) of the OP-1 responsive transcription inhibitory element resulted in a loss of OP-1 responsiveness (Example 5). Specifically, a C/EBPα mutant (SEQ ID NO. 9) and an E-box mutant (SEQ ID NO. 10) resulted in a loss of OP-1 mediated down regulation of gene expression. In addition, a CAAT mutant (SEQ ID NO. 7) and a C mutant (SEQ ID NO. 8), also down-regulated gene expression. However, the downregulation of the CAAT and C mutants was not OP-1 mediated.

In another embodiment of this invention, the DNA sequence hybridizes under stringent conditions to any of the sequences described above. One example of a stringent hybridization condition is hybridization in 4× SSC at 65° C. (or 10° C. higher than the calculated melting temperature for a hybrid between the probe and a nucleic acid sequence containing no mis-matched base pairs), followed by washing in 0.1× SSC at the hybridization temperature. Another stringent hybridization condition is hybridization in 50% formamide, 4× SSC at 42° C. (see e.g., T. Maniatis et al., *Molecular Cloning*(*A Laboratory Manual*), Cold Spring Harbor Laboratory, pp. 387–89 (1982)).

The vectors and host cells that are appropriate for evaluating the ability of a test compound to induce a morphogenic protein mediated biological effect are well known in the art. Useful host cells include but are not limited to primary, transformed or immortalized eukaryotic cells in culture, yeasts such as Saccharomyces and Picia, insect-baculovirus cell systems. Preferred eukaryotic host cells are mammalian cells, including human, murine, rat, primate, porcine or hamster cells.

The isolated DNA sequence of this invention comprises a morphogenic protein responsive transcription inhibitory element operably linked to a reporter gene or any other gene of choice encoding a detectable gene product. In one embodiment the DNA sequence further comprises a cloning site for the insertion of a reporter gene or other gene of choice. The insertion of a reporter gene or other gene of choice in the cloning site, operably links the morphogenic protein responsive transcription inhibitory element to the reporter gene or other gene of choice. DNA vector design for transfection into mammalian cells should include appropriate sequences to promote expression of the gene of interest, including: appropriate transcription initiation, termination and enhancer sequences; efficient RNA processing signals such as splicing and polyadenylation signals; sequences that stabilize cytoplasmic mRNA; sequences that enhance translation efficiency (i.e., Kozak consensus sequence); sequences that enhance protein stability; and when desired, sequences that enhance protein secretion. Further details on the technical aspects of preparing the vectors of this invention can be found in a number of texts and laboratory manuals in the art. See, e.g., F. M. Ausubel et al., ed., *Current Protocols in Molecular Biology*, John Wiley & Sons, New York (1989).

Production of Morphogenic Protein Analogs

In one embodiment of this invention any compound capable of mimicking at least one biological effect of a morphogenic protein, regardless of its chemical or biochemical nature, may be used as a morphogenic protein analog. The morphogenic protein analog of this invention may be derived from a variety of sources. Morphogenic protein analogs may be isolated from natural sources, or may be produced by expressing an appropriate DNA molecule in a host cell. In addition, the morphogenic protein analogs of this invention may be derived synthetically. The synthetic morphogenic protein analogs of this invention may be produced according to rational drug design. The synthetic morphogenic protein analogs of this invention may optionally be expressed from a recombinant DNA molecule in a host cell. Moreover, a morphogenic protein analog identified according to the method of the present invention can be produced in commercially useful quantities.

The commercially useful quantities of a morphogenic protein analog according to this invention can be produced using any appropriate method. These methods include, but are not limited to expression and purification from host cells, synthetic processes, fermentation or cell culture.

The host-vector systems that are appropriate for the recombinant expression of morphogenic protein analogs are well known in the art. Useful host cells include but are not limited to bacteria such as E. coli, yeasts such as Saccharomyces and Picia, insect-baculovirus cell systems, and primary, transformed or immortalized eukaryotic cells in culture. Preferred eukaryotic host cells included CHO, COS, and BSC cells.

An appropriate vector is selected according to the host system selected. Useful vectors include but are not limited to plasmids, cosmids, bacteriophage, insect and animal viral vectors including retroviruses, and other single and double-stranded DNA viruses.

In one embodiment of this invention, the morphogenic protein analog may be derived from a recombinant DNA molecule expressed in a prokaryotic host. Using recombinant DNA techniques, various fusion genes have been constructed to induce recombinant expression of naturally-sourced osteogenic sequences in E. coli (see, e.g., Oppermann et al., U.S. Pat. No. 5,354,557, incorporated herein by reference). Using analogous procedures, DNAs encoding naturally-sourced morphogenic protein analogs may be prepared as fusion constructs linked by the acid labile cleavage site (Asp-Pro) to a leader sequence (such as the "MLE leader") suitable for promoting expression in E. coli.

In another embodiment of this invention, the morphogenic protein analog is expressed using a mammalian host/vector system. It may be preferable to recombinantly produce a mammalian protein for therapeutic uses in mammalian cell culture systems in order to produce a protein whose structure resembles more closely that of the natural material. Recombinant protein production in mammalian cells requires the establishment of appropriate cells and cell lines that are easy to transfect, are capable of stably maintaining foreign DNA with an unrearranged sequence, and which have the necessary cellular components for efficient transcription, translation, post-translational modification and secretion of the protein. In addition, a suitable vector carrying the gene of interest is necessary.

DNA vector design for transfection into mammalian cells should include appropriate sequences to promote expression of the gene of interest, including: appropriate transcription initiation, termination and enhancer sequences; efficient RNA processing signals such as splicing and polyadenylation signals; sequences that stabilize cytoplasmic mRNA; sequences that enhance translation efficiency (i.e., Kozak consensus sequence); sequences that enhance protein stability; and when desired, sequences that enhance protein secretion.

Preferred DNA vectors also include a marker gene and means for amplifying the copy number of the gene of interest. DNA vectors may also comprise stabilizing sequences (e.g., ori- or ARS-like sequences and telomere-like sequences), or may alternatively be designed to favor directed or non-directed integration into the host cell genome.

Substantial progress in the development of mammalian cell expression systems has been made in the last decade and many aspects of the system are well characterized. A detailed review of the production of foreign proteins in mammalian cells, including useful cells, protein expression-promoting sequences, marker genes, and gene amplification methods, is disclosed in M. M. Bendig, *Genetic Engineering*, 7, pp. 91–127 (1988).

Particular details of the transfection, expression and purification of recombinant proteins are well documented and are understood by those of skill in the art. Further details on the various technical aspects of each of the steps used in recombinant production of foreign genes in mammalian cell expression systems can be found in a number of texts and laboratory manuals in the art. See, e.g., F. M. Ausubel et al., ed., *Current Protocols in Molecular Biology*, John Wiley & Sons, New York (1989).

Briefly, among the best characterized transcription promoters useful for expressing a foreign gene in a particular mammalian cell are the SV40 early promoter, the adenovirus major late promoter (AdMLP), the mouse metallothionein-I promoter (mMT-I), the Rous sarcoma virus (RSV) long terminal repeat (LTR), the mouse mammary tumor virus long terminal repeat (MMTV-LTR), and the human cytomegalovirus major intermediate-early promoter (hCMV). The DNA sequences for all of these promoters are known in the art and are available commercially.

One method of gene amplification in mammalian cell systems is the use of the selectable dihydrofolate reductase (DHFR) gene in a dhfr- cell line. Generally, the DHFR gene is provided on the vector carrying the gene of interest, and addition of increasing concentrations of the cytotoxic drug methotrexate (MTX) leads to amplification of the DHFR gene copy number, as well as that of the physically-associated gene of interest. DHFR as a selectable, amplifiable marker gene in transfected chinese hamster ovary cell lines (CHO cells) is particularly well characterized in the art. Other useful amplifiable marker genes include the adenosine deaminase (ADA) and glutamine synthetase (GS) genes.

In a preferred expression system, gene amplification is further enhanced by modifying marker gene expression regulatory sequences (e.g., enhancer, promoter, and transcription or translation initiation sequences) to reduce the levels of marker protein produced. Lowering the level of DHFR transcription increases the DHFR gene copy number (and the physically-associated gene) to enable the transfected cell to adapt to growth in even low levels of methotrexate (e.g., 0.1 $\mu$M MTX). Preferred expression vectors such as pH754 and pH752 (Oppermann et al., U.S. Pat. No. 5,354,557, FIGS. 19C and D), have been manipulated using standard recombinant DNA technology, to create a weak DHFR promoter. As will be appreciated by those skilled in the art, other useful weak promoters, different from those disclosed and preferred herein, can be constructed using standard vector construction methodologies. In addition, other, different regulatory sequences also can be modified to achieve the same effect.

Another gene amplification scheme relies on the temperature sensitivity (ts) of BSC40-tsA58 cells transfected with an SV40 vector. Temperature reduction to 33° C. stabilizes the temperature sensitive SV40 T antigen, which leads to the excision and amplification of the integrated transfected vector DNA thereby amplifying the physically associated gene of interest.

The choice of cells/cell lines is also important and depends on the needs of the skilled practitioner. Monkey kidney cells (COS) provide high levels of transient gene expression providing a useful means for rapidly testing vector construction and the expression of cloned genes. COS cells are transfected with a simian virus 40 (SV40) vector carrying the gene of interest. The transfected COS cells eventually die, thus preventing the long term production of the desired protein product. However, transient expression does not require the time consuming process required for the development of stable cell lines.

CHO cells are capable of successfully expressing a wide variety of proteins from a broad range of cell types. Thus, while the glycosylation pattern on a recombinant protein produced in a mammalian cell expression system may not be identical to the natural protein, the differences in oligosaccharide side chains are often not essential for biological activity of the expressed protein.

Several different mammalian cell expression systems may be used to express recombinant morphogenic protein analogs according to this invention. Stable cell lines have been developed using CHO cells and a temperature-sensitive (ts) strain of BSC cells (simian kidney cells, BSC40-tsA58; Biotechnology, 6, pp. 1192–96 (1988)) for the long term production of osteogenic protein OP-1. Among established cell lines, CHO cells may be the best characterized to date, and are a preferred cell line for mammalian cell expression of recombinant morphogenic proteins.

Pharmaceutical Compositions

The morphogenic protein analogs of the present invention can be formulated as part of a pharmaceutical composition. The pharmaceutical compositions provided by this invention comprise at least one morphogenic protein analog that is capable of mimicking a biological effect of a morphogenic protein when administered or implanted into a patient. The compositions of this invention will be administered at an effective dose to induce the particular type of tissue at the treatment site selected according to the particular clinical condition addressed. Determination of a preferred pharmaceutical formulation and a therapeutically effective dose regimen for a given application is well within the skill of the art taking into consideration, for example, the mode of administration, the condition and weight of the patient, the extent of the desired treatment and the tolerance of the patient for the treatment.

Administration of the morphogenic protein analogs of this invention, including isolated and purified forms of morphogenic protein analogs, their salts or pharmaceutically acceptable derivatives thereof, may be accomplished using any of the conventional modes of administration.

The pharmaceutical compositions comprising a morphogenic protein analog of this invention may be in a variety of forms. These include, for example, solid, semi-solid and liquid dosage forms such as tablets, pills, powders, liquid solutions or suspensions, suppositories, and injectable and infusible solutions. The preferred form depends on the intended mode of administration and therapeutic application and may be selected by one skilled in the art. Modes of administration may include oral, parenteral, subcutaneous, intravenous, intralesional or topical administration. In most cases, the pharmaceutical compositions of this invention will be administered in the vicinity of the treatment site in need of tissue regeneration or repair.

The pharmaceutical compositions comprising a morphogenic protein analog of this invention may, for example, be placed into sterile, isotonic formulations with or without cofactors which stimulate uptake or stability. The formulation is preferably liquid, or may be lyophilized powder. For example, the morphogenic protein analog of this invention may be diluted with a formulation buffer comprising 5.0 mg/ml citric acid monohydrate, 2.7 mg/ml trisodium citrate, 41 mg/ml mannitol, 1 mg/ml glycine and 1 mg/ml polysorbate 20. This solution can be lyophilized, stored under refrigeration and reconstituted prior to administration with sterile Water-For-Injection (USP).

The compositions also will preferably include conventional pharmaceutically acceptable carriers well known in the art (see for example Remington's Pharmaceutical Sciences, 16th Edition, 1980, Mac Publishing Company). Such pharmaceutically acceptable carriers may include other medicinal agents, carriers, genetic carriers, adjuvants, excipients, etc., such as human serum albumin or plasma preparations. The compositions are preferably in the form of a unit dose and will usually be administered as a dose regimen that depends on the particular tissue treatment.

The pharmaceutical compositions of this invention may also be administered in conjunction with a morphogenic device using, for example, microspheres, liposomes, other microparticulate delivery systems or sustained release formulations placed in, near, or otherwise in communication with affected tissues or the bloodstream bathing those tissues (see morphogenic devices, below).

Liposomes containing a morphogenic protein analog of this invention can be prepared by well-known methods (See, e.g. DE 3,218,121; Epstein et al., Proc. Natl. Acad. Sci. U.S.A., 82, pp. 3688–92 (1985); Hwang et al., Proc. Natl. Acad. Sci. U.S.A., 77, pp. 4030–34 (1980); U.S. Pat. Nos. 4,485,045 and 4,544,545). Ordinarily the liposomes are of the small (about 200–800 Angstroms) unilamellar type in which the lipid content is greater than about 30 mol. % cholesterol. The proportion of cholesterol is selected to control the optimal rate of morphogenic protein analog release.

The morphogenic protein analogs of this invention may also be attached to liposomes containing other biologically active molecules such as immunosuppressive agents, cytokines, etc., to modulate the rate and characteristics of tissue induction. Attachment of morphogenic protein analogs to liposomes may be accomplished by any known cross-linking agent such as heterobifunctional cross-linking agents that have been widely used to couple toxins or chemotherapeutic agents to antibodies for targeted delivery. Conjugation to liposomes can also be accomplished using the carbohydrate-directed cross-linking reagent 4-(4-maleimidophenyl) butyric acid hydrazide (MPBH) (Duzgunes et al., J. Cell. Biochem. Abst. Suppl. 16E 77 (1992)).

Morphogenic Devices

The morphogenic protein analogs of the present invention may also be included in morphogenic devices. The morphogenic devices of this invention comprise a morphogenic protein analog dispersed in an implantable biocompatible carrier material that functions as a suitable delivery or support system for the compounds. Suitable examples of sustained release carriers include semipermeable polymer matrices in the form of shaped articles such as suppositories or capsules. Implantable or microcapsular sustained release matrices include polylactides (U.S. Pat. No. 3,773,319; EP 58,481), copolymers of L-glutamic acid and ethyl-L-glutamate (Sidman et al., *Biopolymers*, 22, pp. 547–56 (1985)); poly(2-hydroxyethyl-methacrylate) or ethylene vinyl acetate (Langer et al., *J. Biomed. Mater. Res.*, 15, pp. 167–277 (1981); Langer, *Chem. Tech.*, 12, pp. 98–105 (1982)).

In one embodiment of this invention, the carrier of the morphogenic device comprises a biocompatible matrix made up of particles or porous materials. The pores are preferably of a dimension to permit progenitor cell migration and subsequent differentiation and proliferation. Various matrices known in the art can be employed (see, e.g., U.S. Pat. Nos. 4,975,526; 5,162,114; 5,171,574 and WO 91/18558, which are herein incorporated by reference).

The particle size should be within the range of 70 $\mu$m–850 $\mu$m, preferably 70 $\mu$m–420 $\mu$m, most preferably 150 $\mu$m–420 $\mu$m. The matrix may be fabricated by close packing particulate material into a shape spanning the particular tissue defect to be treated. Alternatively, a material that is biocompatible, and preferably biodegradable in vivo may be structured to serve as a temporary scaffold and substratum for recruitment of migratory progenitor cells, and as a base for their subsequent anchoring and proliferation.

Useful matrix materials comprise, for example, collagen; homopolymers or copolymers of glycolic acid, lactic acid, and butyric acid, including derivatives thereof; and ceramics, such as hydroxyapatite, tricalcium phosphate and other calcium phosphates. Various combinations of these or other suitable matrix materials also may be useful as determined by the assays set forth herein.

Currently preferred carriers include particulate, demineralized, guanidine-extracted, species-specific (allogenic) bone, and specially treated particulate, protein-extracted, demineralized xenogenic bone. Optionally, such xenogenic bone powder matrices also may be treated with proteases such as trypsin. Preferably, the xenogenic matrices are treated with one or more fibril modifying agents to increase the intraparticle intrusion volume (porosity) and surface area. Useful modifying agents include solvents such as dichloromethane, trichloroacetic acid, acetonitrile and acids such as trifluoroacetic acid and hydrogen fluoride. The currently preferred fibril-modifying agent useful in formulating the matrices of this invention is a heated aqueous medium, preferably an acidic aqueous medium having a pH less than about pH 4.5, most preferably having a pH within the range of about pH 2-pH 4. A currently preferred heated acidic aqueous medium is 0.1% acetic acid which has a pH of about 3. Heating demineralized, delipidated, guanidine-extracted bone collagen in an aqueous medium at elevated temperatures (e.g., in the range of about 37° C.–65° C., preferably in the range of about 45° C.–60° C.) for approximately one hour generally is sufficient to achieve the desired surface morphology. Although the mechanism is not clear, it is hypothesized that the heat treatment alters the collagen fibrils, resulting in an increase in the particle surface area.

Demineralized guanidine-extracted xenogenic bovine bone comprises a mixture of additional materials that may be fractionated further using standard biomolecular purification techniques. For example, chromatographic separation of extract components followed by addition back to active matrix of the various extract fractions corresponding to the chromatogram peaks may be used to improve matrix properties by fractionating away inhibitors of bone or tissue-inductive activity.

The matrix may also be substantially depleted in residual heavy metals. Treated as disclosed herein, individual heavy metal concentrations in the matrix can be reduced to less than about 1 ppm.

One skilled in the art may create a biocompatible matrix of choice having a desired porosity or surface microtexture useful in the production of morphogenic devices to promote bone or other tissue induction, or as a biodegradable sustained release implant. In addition, synthetically formulated matrices, prepared as disclosed herein, may be used.

General Consideration of Matrix Properties

The currently preferred carrier material is a xenogenic bone-derived particulate matrix treated as described herein. This carrier may be replaced by either a biodegradable-synthetic or a synthetic-inorganic matrix (e.g., hydroxyapatite (HAP), collagen, carboxymethyl-cellulose, tricalcium phosphate or polylactic acid, polyglycolic acid, polybutyric acid and various copolymers thereof.)

Matrix geometry, particle size, the presence of surface charge, and the degree of both intra- and inter-particle porosity are all important to successful matrix performance. Studies have shown that surface charge, particle size, the presence of mineral, and the methodology for combining matrix and morphogenic protein analogs all play a role in achieving successful tissue induction.

The sequential cellular reactions in the interface of the bone matrix/osteogenic protein implants are complex. The multistep cascade includes: binding of fibrin and fibronectin to implanted matrix, migration and proliferation of mesenchymal cells, differentiation of the progenitor cells into chondroblasts, cartilage formation, cartilage calcification, vascular invasion, bone formation, remodeling, and bone marrow differentiation.

A successful carrier for morphogenic protein analogs should perform several important functions. It should act as a slow release delivery system of morphogenic protein analog, protect the morphogenic protein analog from nonspecific proteolysis, and should accommodate each step of the cellular responses involved in progenitor cell induction during tissue development.

In addition, selected materials must be biocompatible in vivo and preferably biodegradable; the carrier preferably acts as a temporary scaffold until replaced completely by new bone or tissue. Polylactic acid (PLA), polyglycolic acid (PGA), and various combinations have different dissolution rates in vivo. In bones, the dissolution rates can vary according to whether the implant is placed in cortical or trabecular bone.

The preferred osteogenic device matrix material, prepared from xenogenic bone and treated as disclosed herein, produces an implantable material useful in a variety of clinical settings. In addition to its use as a matrix for bone formation in various orthopedic, periodontal, and reconstructive procedures, the matrix also may be used as a sustained release carrier, or as a collagenous coating for orthopedic or general prosthetic implants.

The matrix may be shaped as desired in anticipation of surgery or shaped by the physician or technician during surgery. It is preferred to shape the matrix to span a tissue defect and to take the desired form of the new tissue. In the case of bone repair of a non-union defect, for example, it is desirable to use dimensions that span the non-union. Rat studies show that the new bone is formed essentially having the dimensions of the device implanted. Thus, the material may be used for topical, subcutaneous, intraperitoneal, or intramuscular implants. In bone formation procedures, the material is slowly absorbed by the body and is replaced by bone in the shape of or very nearly the shape of the implant.

The matrix may comprise a shape-retaining solid made of loosely-adhered particulate material, e.g., collagen. It may also comprise a molded, porous solid, or simply an aggregation of close-packed particles held in place by surrounding tissue. Masticated muscle or other tissue may also be used. Large allogenic bone implants can act as a carrier for the matrix if their marrow cavities are cleaned and packed with particles comprising dispersed morphogenic protein analog. The matrix may also take the form of a paste or a hydrogel.

When the carrier material comprises a hydrogel matrix, it refers to a three dimensional network of cross-linked hydrophilic polymers in the form of a gel substantially composed of water, preferably but not limited to gels being greater than 90% water. Hydrogel matrices can carry a net positive or net negative charge, or may be neutral. A typical net negative charged matrix is alginate. Hydrogels carrying a net positive charge may be typified by extracellular matrix components such as collagen and laminin. Examples of commercially available extracellular matrix components include Matrigel™ and Vitrogen™. An example of a net neutral hydrogel is highly crosslinked polyethylene oxide, or polyvinylalcohol.

Various growth factors, cytokines, hormones, trophic agents and therapeutic compositions including antibiotics and chemotherapeutic agents, enzymes, enzyme inhibitors and other bioactive agents also may be adsorbed onto or dispersed within the carrier material comprising the morphogenic protein analog, and will also be released over time at the implantation site as the matrix material is slowly absorbed.

Other Tissue-Specific Matrices

In addition to the naturally-derived bone matrices described above, useful matrices may also be formulated synthetically by adding together reagents that have been appropriately modified. One example of such a matrix is the porous, biocompatible, in vivo biodegradable synthetic matrix disclosed in WO91/18558, the disclosure of which is hereby incorporated by reference.

Briefly, the matrix comprises a porous crosslinked structural polymer of biocompatible, biodegradable collagen, most preferably tissue-specific collagen, and appropriate, tissue-specific glycosaminoglycans as tissue-specific cell attachment factors. Bone tissue-specific collagen (e.g., Type I collagen) derived from a number of sources may be suitable for use in these synthetic matrices, including soluble collagen, acid-soluble collagen, collagen soluble in neutral or basic aqueous solutions, as well as those collagens which are commercially available. In addition, Type II collagen, as found in cartilage, also may be used in combination with Type I collagen.

Glycosaminoglycans (GAGs) or mucopolysaccharides are polysaccharides made up of residues of hexoamines glycosidically bound and alternating in a more-or-less regular manner with either hexouronic acid or hexose moieties. GAGs are of animal origin and have a tissue specific distribution (see, e.g., Dodgson et al., in *Carbohydrate Metabolism and its Disorders*, Dickens et al., eds., Vol. 1, Academic Press (1968)). Reaction with the GAGs also provides collagen with another valuable property, i.e., inability to provoke an immune reaction (foreign body reaction) from an animal host.

Useful GAGs include those containing sulfate groups, such as hyaluronic acid, heparin, heparin sulfate, chondroitin 6-sulfate, chondroitin 4-sulfate, dermatan sulfate, and keratin sulfate. For osteogenic devices, chondroitin 6-sulfate currently is preferred. Other GAGs also may be suitable for forming the matrix described herein, and those skilled in the art will either know or be able to ascertain other suitable GAGs using no more than routine experimentation. For a more detailed description of mucopolysaccharides, see Aspinall, Polysaccharides, Pergamon Press, Oxford (1970).

Collagen can be reacted with a GAG in aqueous acidic solutions, preferably in diluted acetic acid solutions. By adding the GAG dropwise into the aqueous collagen dispersion, coprecipitates of tangled collagen fibrils coated with GAG results. This tangled mass of fibers then can be homogenized to form a homogeneous dispersion of fine fibers and then filtered and dried.

Insolubility of the collagen-GAG products can be raised to the desired degree by covalently cross-linking these materials, which also serves to raise the resistance to resorption of these materials. In general, any covalent G60 cross-linking method suitable for cross-linking collagen also is suitable for cross-linking these composite materials, although cross-linking by a dehydrothermal process is preferred.

When dry, the cross-linked particles are essentially spherical with diameters of about 500 μm. Scanning electron microscopy shows pores of about 20 μm on the surface and 40 μm on the interior. The interior is made up of both fibrous and sheet-like structures, providing surfaces for cell attachment. The voids interconnect, providing access to the cells throughout the interior of the particle. The material appears to be roughly 99.5% void volume, making the material very efficient in terms of the potential cell mass that can be grown per gram of microcarrier.

Another useful synthetic matrix is one formulated from biocompatible, in vivo biodegradable synthetic polymers, such as those composed of glycolic acid, lactic acid and/or butyric acid, including copolymers and derivatives thereof. These polymers are well described in the art and are available commercially. For example, polymers composed of polylactic acid (e.g., MW 100 ka), 80% polylactide/20% glycoside or poly 3-hydroxybutyric acid (e.g., MW 30 ka) all may be purchased from PolySciences, Inc. The polymer compositions generally are obtained in particulate form and the morphogenic devices preferably fabricated under non-aqueous conditions (e.g., in an ethanol-trifluoroacetic acid solution, EtOH/TFA) to avoid hydrolysis of the polymers. In addition, one can alter the morphology of the particulate polymer compositions, for example to increase porosity, using any of a number of particular solvent treatments known in the art.

Prosthetic Devices

In another embodiment of this invention, an implantable prosthetic device comprising a morphogenic protein analog is provided. Any prosthetic implant selected for a particular treatment by the skilled practitioner may be used in combination with a composition comprising at least one morphogenic protein analog according to this invention. The prosthesis may be made from a material comprising metal or ceramic. Preferred prosthetic devices are selected from the group consisting of a hip device, a screw, a rod and a titanium cage for spine fusion.

The morphogenic composition is disposed on the prosthetic implant on a surface region that is implantable adjacent to a target tissue in the mammal. Preferably, the mammal is a human patient. The composition is disposed on the surface of the implant in an amount sufficient to promote enhanced tissue growth into the surface. The amount of the composition sufficient to promote enhanced tissue growth may be determined empirically by those of skill in the art using bioassays such as those described herein and in Rueger et al., U.S. Pat. No. 5,344,654, which is incorporated herein by reference. Preferably, animal studies are performed to optimize the concentration of the composition components before a similar prosthetic device is used in the human patient. Such prosthetic devices will be useful for repairing orthopedic defects, injuries or anomalies in the treated mammal.

Thus this invention also provides a method for promoting in vivo integration of an implantable prosthetic device into a target tissue of a mammal comprising the steps of providing on a surface of the prosthetic device a composition comprising at least one osteogenic protein analog, and implanting the device in a mammal at a locus where the target tissue and the surface of the prosthetic device are maintained at least partially in contact for a time sufficient to permit enhanced tissue growth between the target tissue and the device.

The following are examples which illustrate the morphogenic protein analog compositions and methods of this invention. These examples should not be construed as limiting: the examples are included for purposes of illustration and the present invention is limited only by the claims.

EXAMPLE 1

Construction of Rat IGFBP-5 Promoter-luciferase Genes

A 1 kb DNA fragment, comprising nucleotides from 888 bp upstream to 114 bp (nucleotides 1–1002 of SEQ ID NO. 1) downstream from the transcription start site (+1) of the rat IGFBP-5 gene was generated by PCR using genomic DNA isolated from rat liver. The sense is 5'AGG ATC TGC CTG CCC TGT3' (SEQ ID NO. 2), and the antisense primer is 5'ACC GAG GAG GGG GAT AAC 3' (SEQ ID NO. 3). Reaction was for 25 cycles at 94° C. for 30 sec; 55° C. for 30 sec; 68° C. for 60 sec; with a final extension at 68° C. for 10 min. The PCR product was directly cloned into the pCRII-TOPO vector (Invitrogen, Carlsbad, Calif.). The clone containing the sense (positive) orientation of the IGFBP-5 promoter was confirmed by restriction enzyme mapping and double stranded DNA sequencing. The IGFBP-5 promoter fragment was then subcloned into the Sac I and Xho I sites of the pGL2-Basic vector (Promega) containing the promoterless luciferase reporter gene (Luc). The antisense fragment of the IGFBP-5 promoter was ligated into the Xho I and Hind III sites of the pGL2-Basic vector. All plasmids were checked for purity on 1% agarose gels. Only the ultrapure DNA preparations were used for transfection studies.

EXAMPLE 2

Generation of Rat IGFBP-5 Promoter Mutants

Deletions in the 5' end of the rat IGFBP-5 promoter were generated by digestion of the plasmid containing the 1 kb promoter fragment with unique restriction enzymes or by PCR (FIG. 3) Constructs with 5' end beginning at position −390, −297, −151, −131, −71, and +32 were generated by digestion of the parent plasmid with Acc I, AlwNI, Stu I, Dra III, Sac I and Dra I, respectively. Constructs with 5' end beginning at position −50 and −33 were generated by PCR using sense primers 5'TGG CAG CCA GGG GCC GTC3' (SEQ ID NO. 4) and 5'CTA TTT AAA AGC GCC TGC3' (SEQ ID NO. 5), respectively. PCR conditions were 35 cycles at 94° C. for 60 sec; 50° C. for 60 sec; 72° C. for 60 sec; and a final extension at 72° C. for 10 min. The resultant DNA fragments were subcloned into the pGL-2-Basic vector. The internal mutations within the 21 bp sequence of the promoter were generated by PCR with sequence-specific oligonucleotide primers (FIG. 5B) and wild-type DNA template (−71/+114) as described above. Alternatively, the QuikChange Site Directed Mutagenesis Kit (Stratagene, LaJolla, Calif.) was used. The DNA products were sequenced in their entirety to ensure the absence of unintended mutations.

EXAMPLE 3

FRC Culture and Transient Transfections

Primary fetal calvarial (FRC) cells were prepared using published procedures (L-C. C. Yeh et al., *Endocrinology*, 138, 4181–4190 (1997), M. A. Aronow et al., *J. Cell Physiol.*, 143, pp. 213–221 (1990); T. K. McCarthy et al.,*J. Bone Miner. Res.*, 3, pp. 401–8 (1988)). Briefly, cells were harvested by sequential collagenase digestions of the calvarium and cells from digestions III to V were pooled. Fetal rat calvaria (FRC) cells were plated in complete medium (MEM, alpha; GIBCO/BRL, Grand Island, N.Y.) containing 10% fetal bovine serum, vitamin C (100 $\mu$g/ml), and antibiotics (100 U/ml penicillin, and 100 mg/ml streptomycin). Cultures were incubated at 37° C. with 95% air/5% $CO_2$ for several days to reach confluence. Cells were then subcultured for experimentations.

Confluent cells of passage 3 were used for experimentation. Transfection studies were carried out using published procedures (L-C. C. Yeh et al., *J. Cell Physiol.*, 175, 78–88 (1998)). Briefly, FRC cells were grown in six-well plates to about 70% confluence in complete αMEM plus serum and were transiently transfected with promoter constructs by the calcium phosphate-DNA coprecipitation method (C. Chen et al. Mol. Cell. Biol., 7, 2745–2752). Plasmid DNA (12 $\mu$g) was used for each six well plate. The medium was removed after 3 hours of transfection and the cells were treated with 15% glycerol/1× HEPES-buffered saline for 2 min at room temperature. Transfected FRC cells were incubated overnight in fresh complete αMEM, followed by treatment with OP-1 (300 ng/ml) or vehicle in serum-free AMEM for 24 h. The IGFBP-5 promoter activity was determined by measuring the luciferase reporter gene activity described in L-C. C. Yeh et al., *J. Cell. Physiol.* 175, 78–88 (1998)). Cells were lysed and an aliquot (20 $\mu$l) was used to measure the luciferase activity using Promega's Luciferase assay kit and the OPTOCOMP I luminometer ILA911 (Tropix). Another aliquot (10 $\mu$l) was used to determine the transfection efficiency by measuring the β-galactosidase activity using the Tropix Galacto-Light kit. The luciferase activity was normalized to the β-galactosidase activity. In some experiments, the Dual-Light Reporter System was used. The system is a chemiluminescent reporter gene assay system for the combined luciferase and β-galactosidase using as substrates luciferin and Galacton-Plus, respectively. Values obtained were comparable to those using the single enzyme system.

EXAMPLE 4

Gel Mobility Shift Assay

Proteins for the gel mobility shift assays were extracted from control or OP-1 -treated confluent FRC cells using published procedures (N. C. Andrews et al., *Nucl. Acid Res.*, 19, 2499 (1991)). Protein concentration was determined using the Bradford method (M. M. Bradford, Anal. Biochem., 72, 248–254 (1976)). The protein extracts were divided into aliquots and immediately frozen at −80° C. until use. The gel mobility shift experiments were carried out using the BandShift kit. Briefly, radiolabeled double stranded DNAs were produced by annealing complementary oligonucleotides (consisting of the sequence from −71 to −33 and its complementary sequence) followed by treatment with T4 polynuceotide kinase in the presence of [$\gamma$-$^{32}$P]ATP. Varying concentrations of protein extracts were incubated with a fixed amount of radiolabeled DNA probe (5550 cpm) for 20 min at room temperature. Samples were analyzed on 5% non-denaturing polyacrylamide gels in 1× TBE. Gels were dried and radioactive bands were detected and quantified using the PhosphorImage (Molecular Dynamics, Sunnyvale, Calif.) and the ImageQuant software. For the competition experiments, an excess amount (20× to 500×) of unlabeled DNA probe or unrelated EBNA-1 or Oct-1 DNA was included in the reaction.

EXAMPLE 5

Statistical Analysis

Multiple means were compared with a one-way analysis of variance (ANOVA), followed by the Student t-test for paired comparisons with the control. The ANOVA and Student's t-test programs in the PSI-Plot (Poly Software International, Salt Lake City, Utah) for personal computers were used for the analyses.

EXAMPLE 6

Reporter Gene Activity in OP-1 -Treated FRC Cells

Figure 4A:
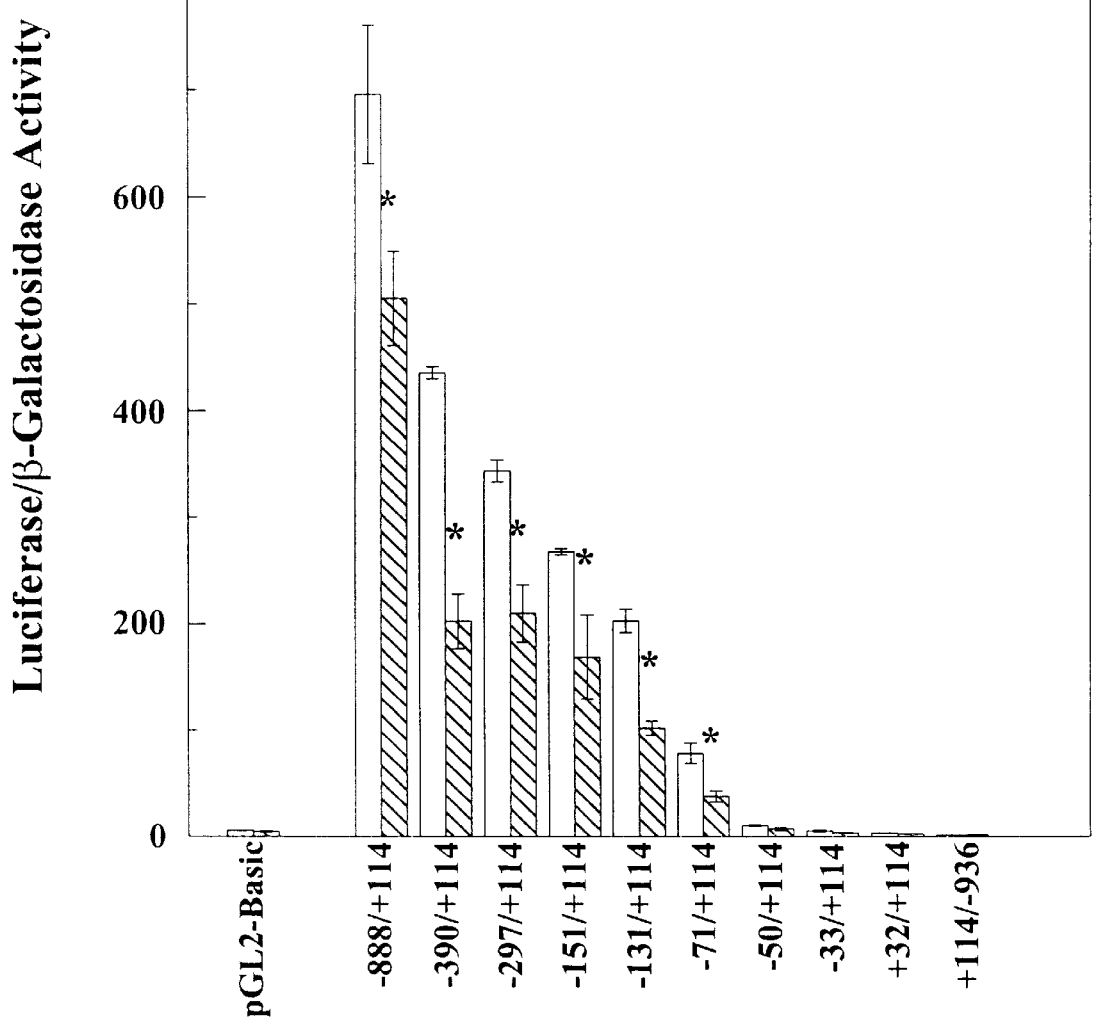
FIGS. 4A and 4B. Effect of OP-1 (300 ng/ml) on IGFBP-5 promoter activity in transiently transfected FRC cells. Cultures were transfected with the DNA constructs containing the different deletions of the IGFBP-5 promoter shown in FIG. 3 and treated with solvent (open bars) or OP-1 (solid bars) for 24 h. (A) The luciferase activity was normalized to the β-galactosidase (β-Gal) activity. Values represent means ± SE of 6 to 10 independent determinations from 3 different FRC preparations. (*) indicates values that are significantly different from control with $p<0.05$. (B) Ratios of normalized luciferase activity in OP-1-treated culture/control culture as a function of different promoter constructs.
Figure 4B:
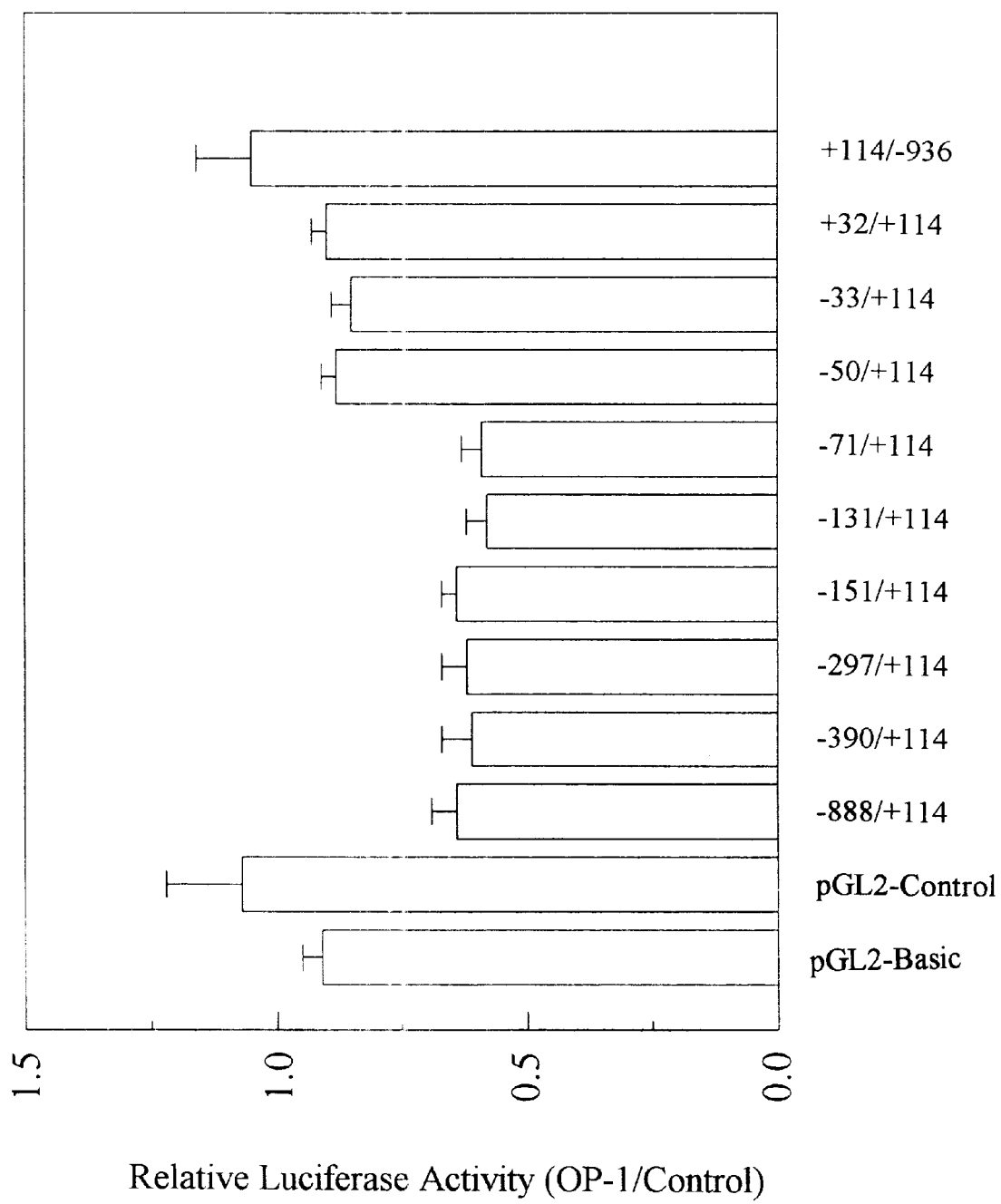

FIG. 4A shows the reporter gene activity of the various clones in FRC cells treated with OP-1 or vehicle. The promoter activity for the pGL2-Basic vector in transfected FRC cells treated with solvent was very low and OP-1 did not affect the promoter activity. The activity of the pGL2-Control vector was high and was slightly elevated in OP-1 treated cells. Sequential removal of the 5' end sequence beginning from −888 resulted in a parallel loss of basal promoter activity, such that the DNA fragment with only 151 bp of the 5' flanking sequence and the first 114 bp of exon 1 retained about 30% of the promoter activity. The DNA fragment with only 156 bp of the 5' flanking sequence and the first 120 bp of exon 1 confers most (61%) of the promoter activity.

EXAMPLE 7

Identifying the Putative Regulatory Elements Responsible for the Down Regulation of Rat IGFBP-5 by OP-1

Figure 5B:
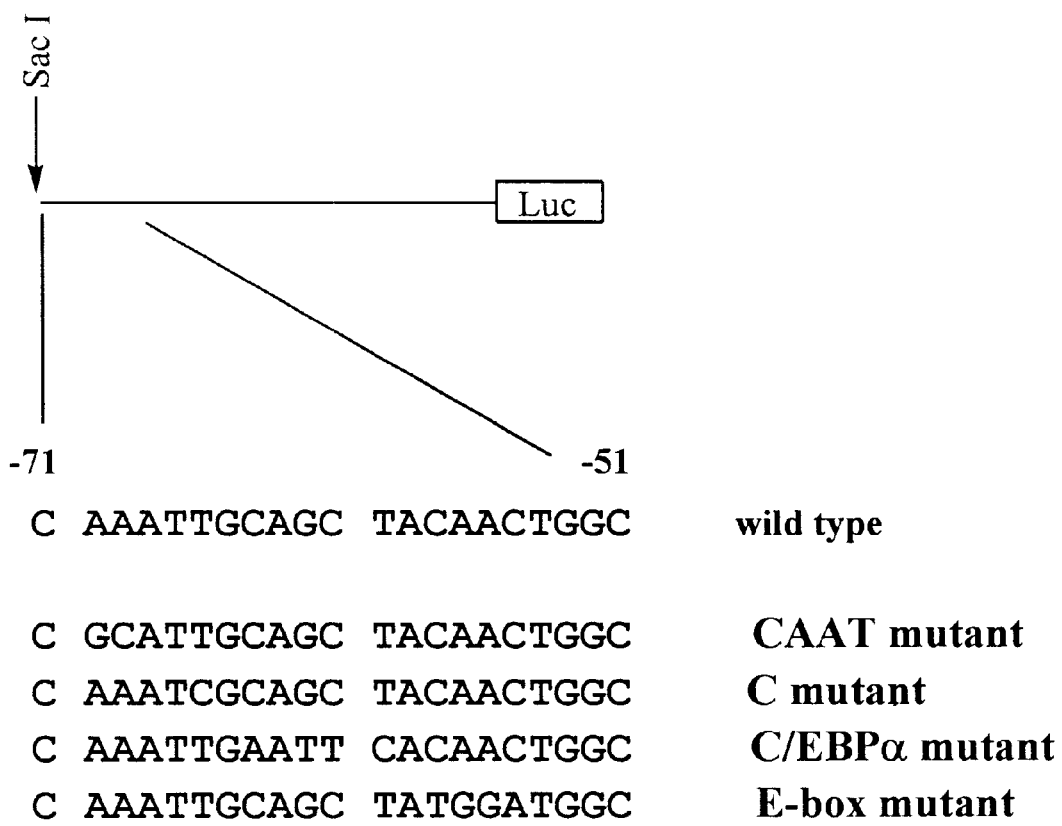
FIG. 5. (A) A partial nucleotide sequence of the IGFBP-5 promoter region of rat, human and mouse. The conserved elements in the region are shown. The region included in the oligonucleotide probe used for gel mobility shift studies is also indicated. (B) Sequences of mutants in the rat IGFBP-5 promoter region used to further define the OP-1 responsive elements.

The region −71 bp to −51 bp contains several putative regulatory transcriptional elements: a CAAT-like sequence, a C/EBPα-like element, and a c-Myb-like (T/CAACG/TG) or E-box-like (CANNTG) motif. These elements are also present in the human and mouse IGFBP-5 promoters (FIG. 5A). To further delineate which one or more of these putative regulatory elements are responsible for the down regulation of the rat IGFBP-5 by OP-1, each of the elements was mutated (see FIG. 5B for sequence). The promoter activity of each mutant was measured following transfection of the FRC cells.

Figure 6A:
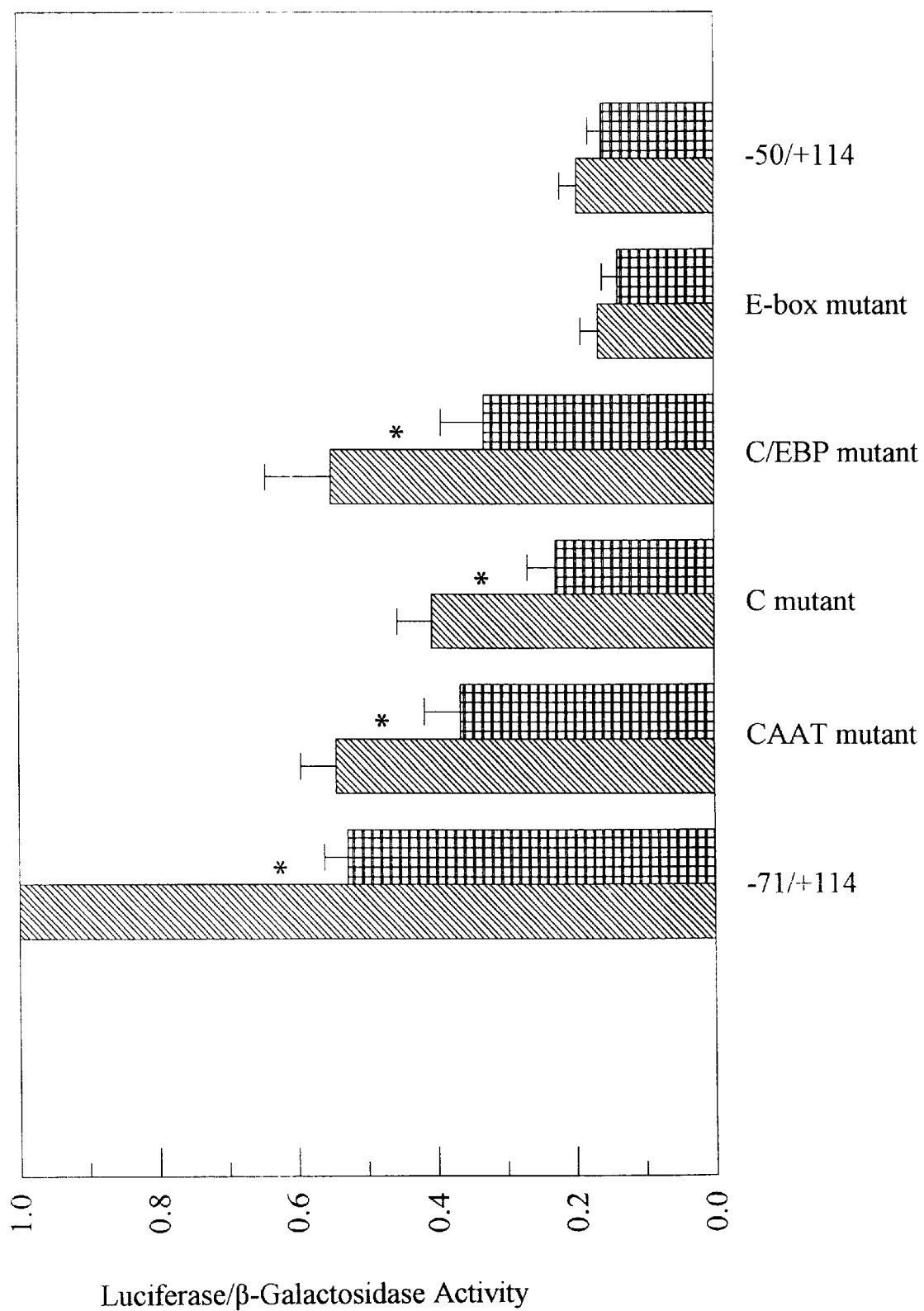
FIGS. 6A and 6B. Effect of OP-1 on the different site-specific mutant IGFBP-5 promoter activity in transiently transfected FRC cells. Cultures were transfected with the different constructs shown in FIG. 5B and treated with solvent or OP-1(300 ng/ml) for 24 h. (A) The luciferase activity was normalized to the β-galactosidase (β-Gal) activity. Values represent means ± SE of 5 to 8 independent determinations from 3 different FRC preparations. (*) indicates values that are significantly different from control with $p<0.01$. (B) Ratios of normalized luciferase activity in OP-1-treated culture/control culture as a function of different promoter constructs.
Figure 6B:
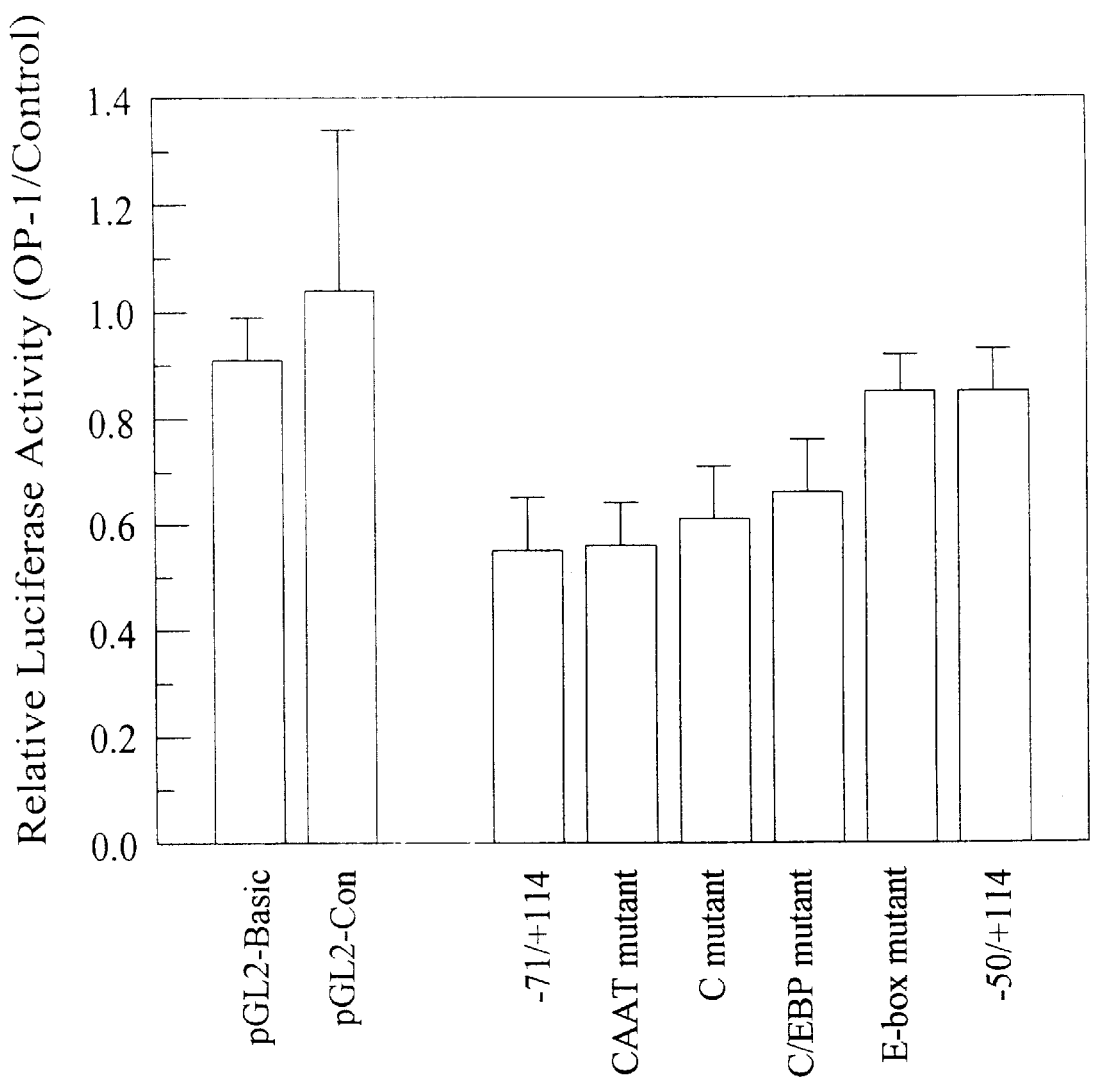

FIG. 6A shows the relative luciferase activity of the various mutant clones in FRC cells treated with OP-1 or vehicle. In agreement with the results shown in FIG. 4, OP-1 dramatically reduced (~47% compared to control) the activity of the IGFBP-5 promoter sequence form −71 to +114 in FRC cells. Mutations in the CAAT-like sequence reduced the promoter activity in both control cells and OP-1-treated cells (FIG. 6A). However, the extent of the reduction in promoter activity induced by OP-1 remained essentially the same (~40%, FIG. 6B). A single T to C mutation or a 4 base mutation with the C/EBPα-like element also reduced the IGFBP-5 promoter activity in both control and OP-1 treated cells (FIG. 6A) and resulted in promoters that were less responsive to OP-1 (FIG. 6B). Mutations in the E-box-like motif reduced the promoter activity in both the control and the OP-1-treated cells (FIG. 6A) and completely abolished the effect of OP-1 (FIG. 6B). These observations suggest that the C/EBPα-like element and the putative E-box-like motif (or at least the CAAC sequence within it) contain cis-acting elements responsible for the down-regulation of IGFBP-5 transcription by OP-1 .

Figure 7:
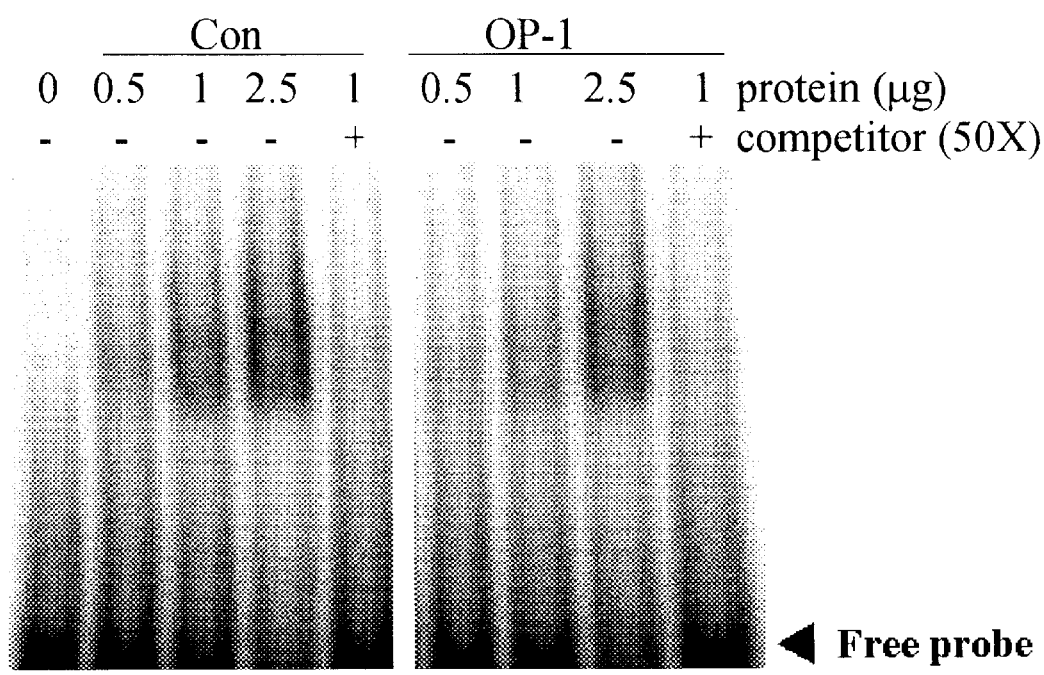
FIG. 7. DNA-protein interactions in the rat IGFBP-5 promoter as revealed by gel-mobility shift assay. The autoradiograph shows results of a representative gel-mobility shift experiment with a $^{32}$P-labeled, double-stranded oligonucleotide spanning nucleotides −71 to −33 of the rat IGFBP-5 promoter and different concentrations of extracts from FRC cells treated with solvent or OP-1 (300 ng/ml).
Figure 8:
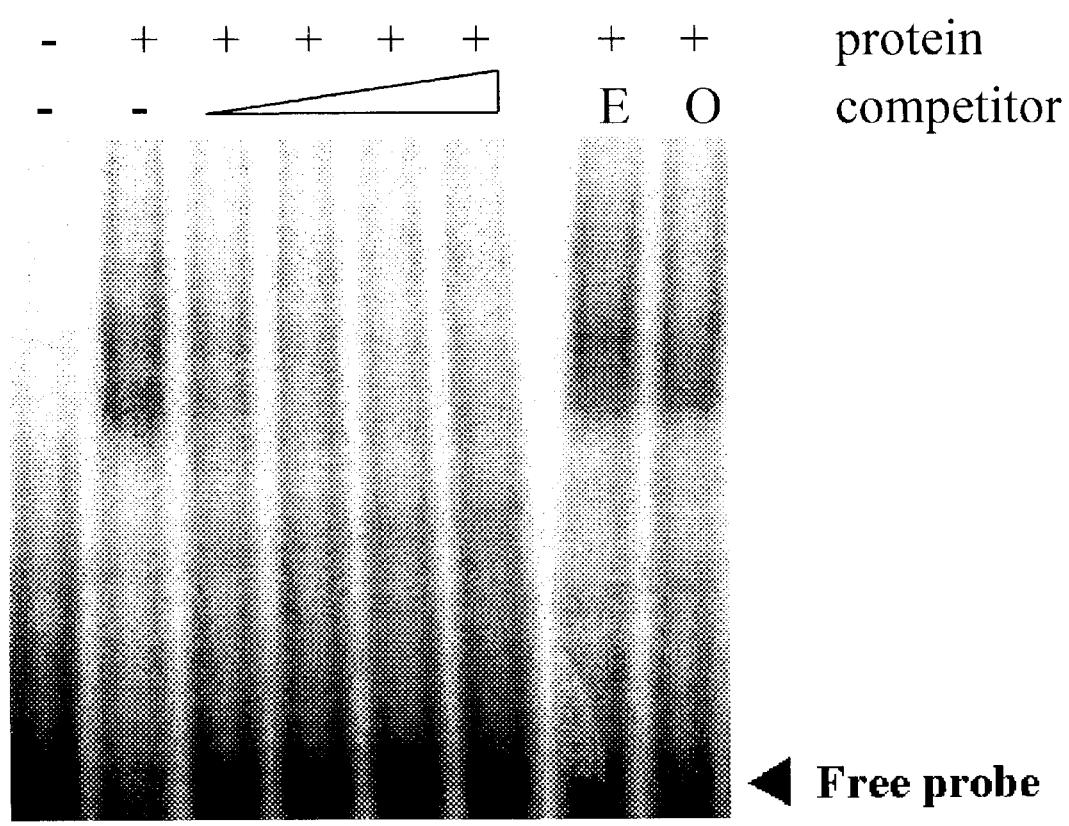
FIG. 8. Specificity of DNA-protein interactions in the rat IGFBP-5 promoter. Gel-mobility shift experiments were conducted as described in FIG. 7, except that different concentrations (20×, 50×, 200× and 500×) of the unlabeled homologous competitor DNA or unlabeled EBNA-1 (E) or Oct-1 (O) DNA was present. All gel-shifted bands were inhibited by homologous competitor DNA in a dose-dependent manner. Band formation was not inhibited by EBNA-1 or Oct-1 DNA.

To examine the role of nuclear proteins in the down-regulation of the IGFBP-5 promoter by OP-1, gel mobility shift assays were carried out using radioactive oligonucleotide probes consisting of the −71/−33 region and proteins from control as well as OP-1-treated FRC cells. FIG. 7 shows the result of a representative gel-shift assay. Two major bands in both the control and OP-1 -treated samples were observed. The intensity of both bands was proportional to the protein concentration and was lower in the OP-1-treated sample (by 30 to 40%) than in the control sample, especially when protein was limiting. The observation would suggest that the concentration of the nuclear protein (s) that interacted with this promoter region was lower in the OP-1 -treated FRC cells than in the control, leading to a decrease in transcription. Such an interpretation is supported by previous observations that OP-1 down-regulates IGFBP-5 transcription. Also the shifted bands were not competed by the unrelated oligonucleotides, EBNA-1 or Oct-1 (FIG. 8).

Figure 9:
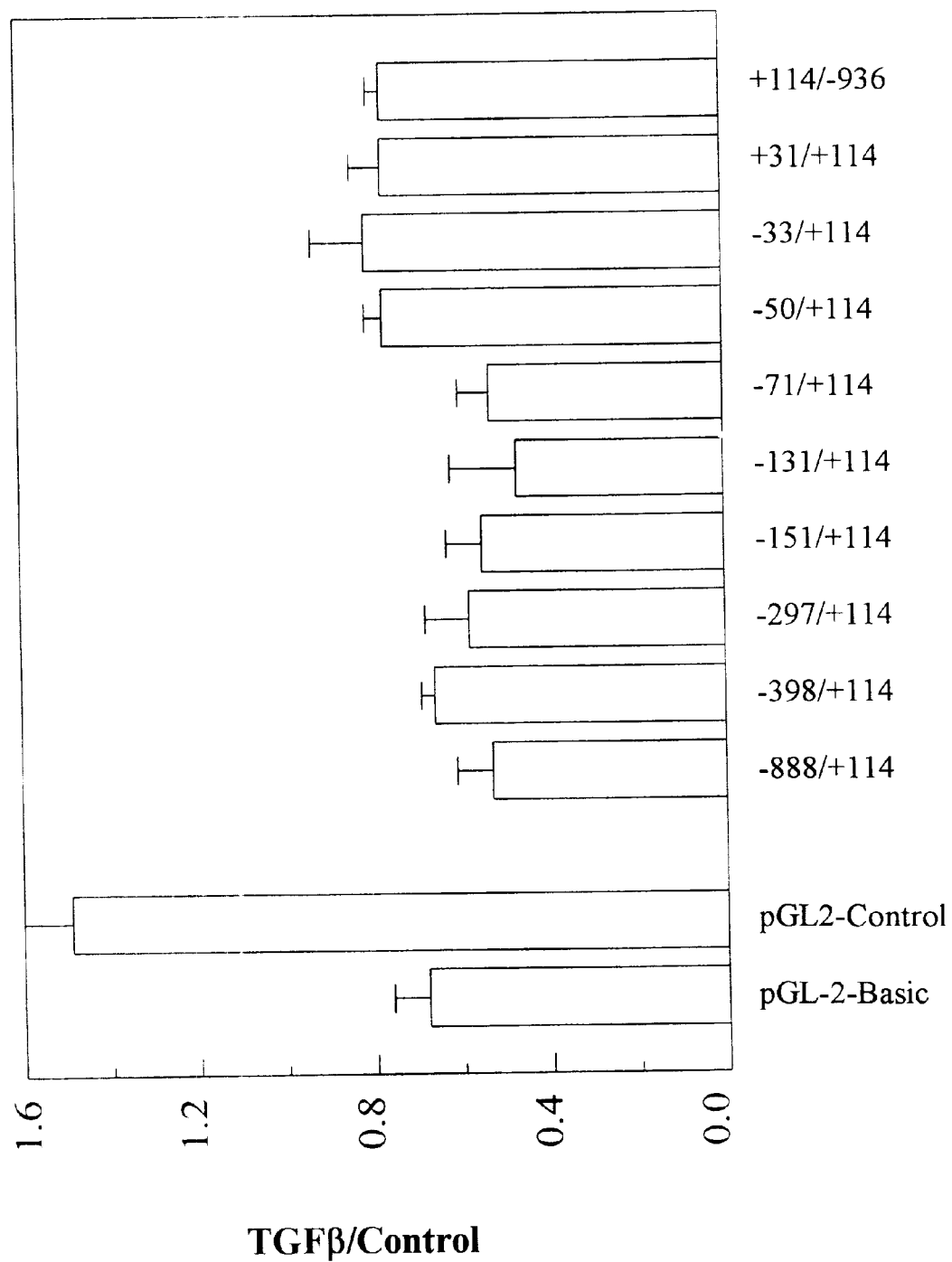
FIG. 9. Effect of TGF-β on IGFBP-5 promoter activity in transiently transfected FRC cells. Cultures were transfected with the different constructs shown in FIG. 3 and treated with TGF-β (2 ng/ml) for 24 h. Values are the relative reporter gene activity (TGF-β/control) and represent mean ± SE of 3 independent determinations using 3 different FRC preparations.

The IGFBP-5 promoter clones were also tested with TGF-β. FIG. 9 shows that TGF-β decreased the IGFBP-5 promoter activity significantly (40–50% compared to the control) in most cases. However, the DNA construct consisting of the −50 to +114 region showed only about 25–30% reduction in IGFBP-5 promoter activity when it was transiently expressed in TGF-β-treated FRC cells compared to control cells. These observations suggest that the 21 bp (−71 to −51) OP-1-responsive region might also respond, though to a lesser extent, to TGF-β.

To further delineate which one or more of the putative regulatory elements are responsible for the down-regulation of the rat IGFBP-5 by TGF-β, the promoter activity of each mutant was measured following transfection of the FRC cells.

Figure 10:
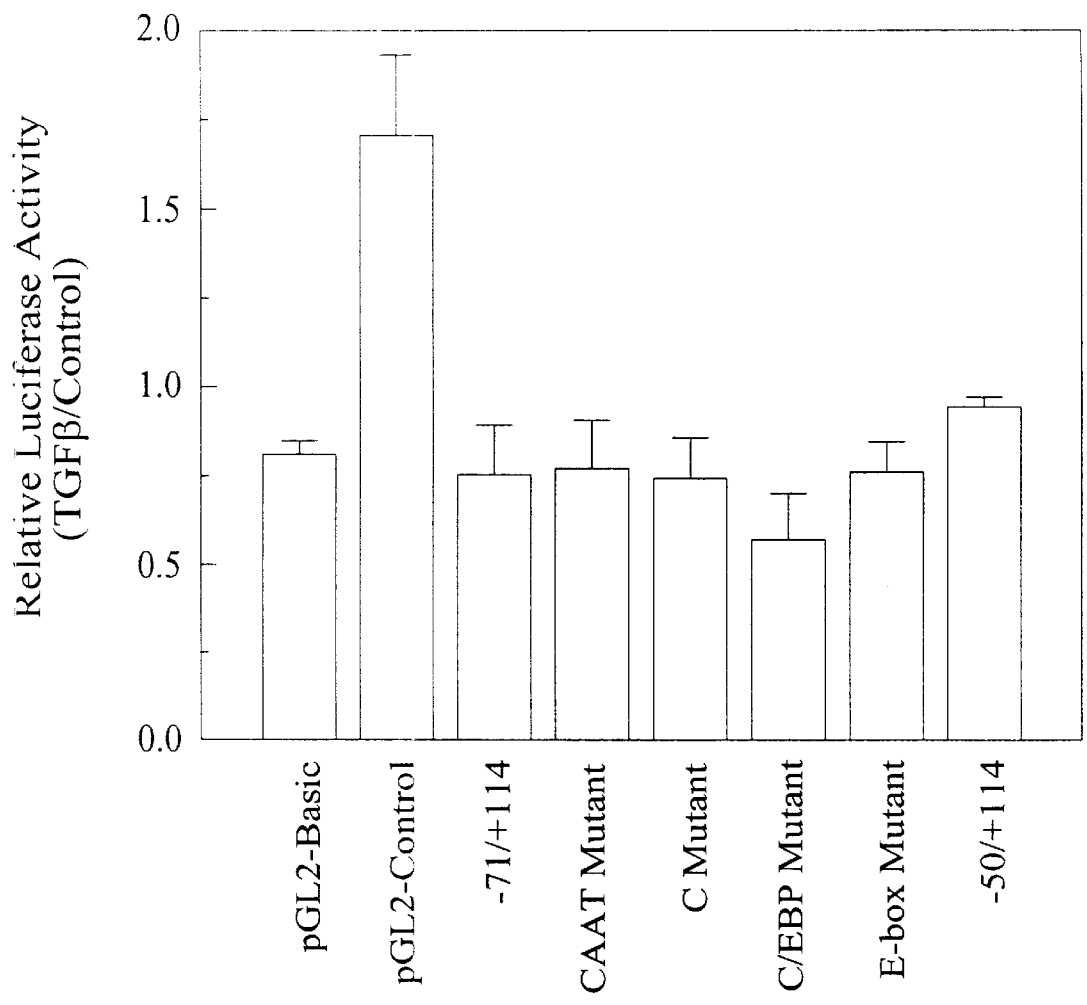
FIG. 10. Effect of TGF-β on the different site-specific mutant IGFBP-5 promoter activity in transiently transfected FRC cells. Cultures were transfected with the different constructs shown in FIG. 5B and treated with solvent or TGF-β (2 ng/ml) for 24 h. Values are the relative reporter gene activity (TGF-β/control) and represent mean ± SE of 5 to 8 independent determinations using 2 different FRC preparations.

FIG. 10 shows the relative luciferase activity of the various mutants clones in FRC cells treated with TGF-β or vehicle. In agreement with the results shown in FIG. 9, TGF-β dramatically reduced (~43% compared to control) the activity of the −71 to +114 promoter region in FRC cells. Mutations in any one of the three putative sites (the CAAT-like sequence, the C/EBPα-like element, or the E-box-like motif) did not abolish the reduction by TGF-β.

EXAMPLE 8

Alkaline Phosphatase (AP) Activity Assay

For measurements of AP activity, confluent FRC cells are treated in 48-well plates as described above. Total cellular AP activity in the lysate is measured using published procedures (Yeh et al. 1996) with p-nitrophenyl phosphate as a substrate in 2-amino-2-methyl-1-propanol buffer, pH 10.3 at 37° C. using a commercial assay kit (Sigma Chemical Co.). Reactions are terminated by the addition of 0.5N NaOH. Absorbance of the reaction mixture is measured at 405 nm using a MRX mcroplate reader (Dynex Technologies, Chantilly, Va.). Protein in the lysates is measured at 590 nm using the MRX microplate reader according to the method of Bradford (1976) with BSA as a standard. AP activity is expressed as nanomoles of p-nitrophenol liberated per ug of total cellular protein.

EXAMPLE 9

Bone Nodule Formation

Confluent FRC cells in 12-well plates are treated in α-MEM containing 5% FBS, ascorbic acid (100 µg/ml), and 5 mM β-glycerol, phosphate (Bellows et al. 1986) with solvent vehicle or OP-1 (200 ng/ml). Media is changed every 3 days. On day 16, cells are rinsed with 1× PBS, fixed in 10% neutral buffered formalin, and finally washed sequentially with ethanol. Mineralized bone nodules are visible as white nodules after fixing and are further confirmed by modified von Kossa staining (Drury and Wallington, 1980). Quantitation of bone nodules is accomplished by capturing the images using an Olympus CK2 inverted microscope (Olympus America, Inc.) equipped with a CCD camera and analyzing the images using the ImagePro Plus Software (Media Cybernetics, Silver Spring, Md.).

The above examples are provided to illustrate the invention but not to limit its scope. Other variants of the invention will be readily apparent to one of ordinary skill in the art and are encompassed by the appended claims. All publications, patents, and patent applications cited herein are hereby incorporated by reference for all purposes.

We claim:

1. A method for identifying a compound capable of inducing a morphogenic protein mediated biological effect, comprising the steps of:
   a) providing a target cell comprising a DNA sequence comprising a morphogenic protein responsive transcription inhibitory element operably linked to a reporter gene or genes encoding a detectable product, wherein the DNA sequence, when present in a morphogenic protein responsive cell exposed to a morphogenic protein, down-regulates transcription of the gene or genes it controls;
   b) exposing the target cell to a test compound; and
   c) comparing the level of production of the detectable product, with the level observed in the absence of the test compound.

2. The method according to claim 1 wherein the morphogenic protein responsive transcription inhibitory element is an OP-1 responsive transcription inhibitory element.

3. The method of claim 2 wherein the OP-1 responsive transcription inhibitory element comprises nucleotides 817–837 of SEQ ID NO. 1.

4. The method according to claim 3 wherein the OP-1 responsive transcription inhibitory element comprises nucleotides 807–847 of SEQ ID NO. 1.

5. The method according to claim 4 wherein the OP-1 responsive transcription inhibitory element comprises nucleotides 799–857 of SEQ ID NO. 1.

6. The method according to any one of claims 1–5 wherein the detectable product is RNA.

7. The method according to any one of claims 1–5 wherein the detectable product is a protein.

8. The method according to claim 1 wherein the morphogenic protein responsive transcription inhibitory element binds a protein capable of binding a C/EBPα-like element, which C/EBPα-like element comprises nucleotides 5–15 of SEQ ID NO. 6.

9. The method according to claim 1 wherein the morphogenic protein responsive transcription inhibitory element binds a protein capable of binding a c-myb motif or a E-box-like motif, said motifs comprising nucleotides 14–20 of SEQ ID NO. 6.

10. The method according to claim 1, wherein the DNA sequence comprising the morphogenic protein responsive transcription inhibitory element is transfected into the target cell.

11. The method according to claim 1, wherein the target cell expresses an OP-1 receptor.

12. The method according to claim 1, further comprising the step of:
   d) detecting the induction by the test compound of a biological effect mediated by a morphogenic protein.

13. The method according to claim 12, wherein the biological effect is selected from the group of an alteration in binding of an intracellular molecule to the morphogenic protein responsive transcription inhibitory element, the induction of phenotypic markers of differentiation, the induction of a progenitor cell to form endochondral or intramembranous bone, the induction of a progenitor cell to form cartilage, or the induction of a progenitor cell to form tissue/ligament-like or neural like tissue.

14. The method according to claim 1, further comprising the step of:
   e) exposing the test compound that induces a level of production of the detectable product that is less than the level observed in the absence of the test compound, to a tissue locus and detecting the ability of the morphogenic protein analog to induce tissue formation in a mammal.

* * * * *

UNITED STATES PATENT AND TRADEMARK OFFICE
CERTIFICATE OF CORRECTION

PATENT NO. : 6,368,787 B1
DATED : April 9, 2002
INVENTOR(S) : Lee-Chuan C. Yeh

It is certified that error appears in the above-identified patent and that said Letters Patent is hereby corrected as shown below:

Title page,
Item [56], under OTHER PUBLICATIONS, in Ji et al., replace "Factor-B-inding" with -- Factor Binding --.

Column 10,
Line 30, delete the second occurrence of "the".

Column 11,
Line 7, replace "morphogeinc" with -- morphogenic --.

Column 24,
Line 40, replace "AMEM" with -- αMEM --.

Column 27,
Line 10, replace "ug" with -- $\mu$g --.

Signed and Sealed this

Twenty-fifth Day of June, 2002

Attest:

*Attesting Officer*

JAMES E. ROGAN
*Director of the United States Patent and Trademark Office*